United States Patent [19]

Chen

[11] Patent Number: 5,428,043

[45] Date of Patent: Jun. 27, 1995

[54] TRICYCLIC-CYCLIC AMINES AS NOVEL CHOLINESTERASE INHIBITORS

[75] Inventor: Yuhpyng L. Chen, Waterford, Conn.

[73] Assignee: Pfizer Inc., New York, N.Y.

[21] Appl. No.: 968,014

[22] Filed: Oct. 29, 1992

Related U.S. Application Data

[63] Continuation-in-part of Ser. No. 639,614, Jan. 10, 1991, abandoned, which is a continuation-in-part of Ser. No. 476,928, Feb. 8, 1990, abandoned.

[51] Int. Cl.$^6$ ............... C07D 211/12; C07D 211/14; C07D 211/10; C07D 241/04; A61K 31/445; A61K 31/505

[52] U.S. Cl. .................... 514/322; 514/255; 514/318; 514/320; 514/321; 514/323; 514/324; 544/359; 544/360; 544/361; 544/366; 544/367; 544/368; 544/373; 544/374; 544/375; 544/378; 546/193; 546/194; 546/197; 546/198; 546/199; 546/200; 546/202; 546/203; 546/204

[58] Field of Search .............. 546/193, 194, 197, 198, 546/199, 200, 202, 203, 204; 544/359, 360, 361, 366, 367, 368, 373, 374, 375, 378; 514/322, 318, 320, 321, 323, 324, 255

[56] References Cited

U.S. PATENT DOCUMENTS

| | | | |
|---|---|---|---|
| 3,910,947 | 10/1975 | Houlihan | 260/309.6 |
| 4,778,812 | 10/1988 | Jirkovsky | 514/323 |
| 4,791,107 | 12/1988 | Hamer et al. | 514/228.2 |
| 4,939,144 | 7/1990 | Coates et al. | 514/212 |
| 5,081,128 | 1/1992 | George et al. | 514/323 |
| 5,096,900 | 3/1992 | George et al. | 514/213 |
| 5,100,901 | 3/1992 | Sugimoto et al. | 514/319 |
| 5,187,165 | 2/1993 | Hamer et al. | 514/307 |

FOREIGN PATENT DOCUMENTS

| | | |
|---|---|---|
| 154864A1 | 9/1985 | European Pat. Off. |
| 170460A1 | 2/1986 | European Pat. Off. |
| 187619A2 | 7/1986 | European Pat. Off. |
| 229391A1 | 7/1987 | European Pat. Off. |
| 296560A2 | 12/1988 | European Pat. Off. |
| 317088A1 | 5/1989 | European Pat. Off. |
| 330026A1 | 8/1989 | European Pat. Off. |
| 351283A1 | 1/1990 | European Pat. Off. |
| 383318A2 | 8/1990 | European Pat. Off. |

OTHER PUBLICATIONS

Abstract for JP 56083471, Fujimoto Seiyaku KK, 4-(-2-hydroxy-isopropyl-amino)-indole prodn. by hydrolysing condensation prod. of 4-hydroxy-indole and 2-oxazolidinone, useful for treating hypertension; 1992.

Derwent Abstract No. 90-218583/29, *Takeda Chemical Ind KK*, New cyclic amine cpds.—useful for therapy of cerebral oedema or apoplexy or as anti-cholinesterase agent (1989).

Becker, Robert E. et al., "Mechanisms of Cholinesterase Inhibition in Senile Dementia of the Alzheimer Type: Clinical, Pharmacological, and Therapeutic Aspects," *Drug Development Research*, 12, pp. 163–195 (1988).

Bolton, Richard E. et al., "Vinyl Azides in Heterocyclic Synthesis. Part 8. Synthesis of the Naturally Occurring Phosphodiesterase Inhibitors PDE-I and PDE-II," *J. Chem. Soc. Perkin Trans.*, 1, pp. 931–935 (1987).

(List continued on next page.)

*Primary Examiner*—Mary C. Lee
*Assistant Examiner*—Joseph K. McKane
*Attorney, Agent, or Firm*—Peter C. Richardson; Gezina Holtrust; B. Timothy Creagan

[57] ABSTRACT

Compounds of the formula

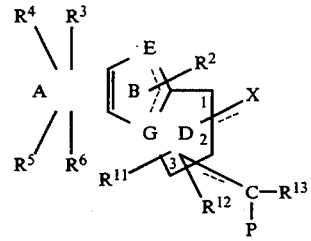

wherein ring A, ring B, ring D, $R^2$, $R^3$, $R^4$, $R^5$, $R^6$, $R^{11}$, $R^{12}$, $R^{13}$, E, G, X and P are as defined below. The compounds of formula I are cholinesterase inhibitors and are useful in enhancing memory in patients suffering from dementia and Alzheimer's disease.

5 Claims, No Drawings

OTHER PUBLICATIONS

Campaigne, E. et al., "Benzo[b]thiophene Derivatives. XIV. Derivatives of Naphtho[1,8-c]thiophene(1)," *J. Heterocyclic Chemistry*, 7, pp. 107-115 (1970).

Casner, Michael L. et al., "Synthesis and Biological Activity of 6-Substituted Mitosene Analogues of the Mitomycins," *J. Med. Chem.*, 28, pp. 921-926 (1985).

Clemo, G. R. et al., "The Chemistry of the Carbazoles. 1:2:3:4-Tetrahydro-4-ketocarbazoles," pp. 700-703 (1951).

Clemo, G. R. et al., "Indene Series. Part I. A Synthesis of 1:2:3:8-Tetrahydro-1-ketocyclopent[a]diene," pp. 863-867 (1951).

Dodd, Robert H. et al., "Hybrid Molecules: Growth Inhibition of Leishmania donovani Promastigotes by Thiosemicarbazones of 3-Carboxy-β-carbolines," *J. Med. Chem.*, 32, pp. 1272-1276 (1989).

Grantham, R. K. et al., "The Formation of Benzimidazolones and Quinoxalines from o-Nitro-phenyldialkylanilines: A Reinvestigation," *J. Chem. Soc.*, pp. 70-74 (1969).

Heath-Brown, B. et al., "Studies in the Indoles Series. Part III. The Japp-Klingemann Reaction," pp. 7185-7193 (1965).

Hoechst, P. et al., "1,2-Cyclisierungsreaktionen an Indolderivaten, 4. Mitt. Zur. Synthese von 1-Oxo-9-methyl-pyrrolo-[1,2-a]indol," *Arch. Pharmaz.*, 8, pp. 779-782 (1975).

Horaguchi, Takaaki et al., "Furan Derivatives. II. The Cyclization of 3-(Benzofuran-3-yl)-propionic Acid Derivatives," *Bulletin of the Chemical Society of Japan*, 49 (3), pp. 737-740 (1976).

Hurd, Charles D. et al., "Friedel-Crafts Reactions of Some Acylals," pp. 1321-1324 (1959).

Iida, Hideo et al., "Intramolecular Cyclization of Enaminones Involving Aryllpalladium Complexes. Synthesis of Carbazoles," *J. Org. Chem.*, 45, pp. 2938-2942 (1980).

Kagechika, Hiroyuki et al., "Retinobenzoic Acids. 3. Structure-Activity Relationships of Retinoidal Azobenzene-4-carboxylic Acids and Stilbene-4-carboxylic Acids," *J. Med. Chem.*, 32, pp. 1098-1108 (1989).

Kametani; Tetsuji et al., "Synthesis of 1-Benzazocin-5-One Derivatives From a 1,2,3,4-Tetrahydrocyclopent[b]Indole; A Synthetic Approach to Mitomycines," *Heterocycles*, 12, No. 7, pp. 913-916 (1979).

Rydon, H. N. et al., "Experiments on the Synthesis of Bz-Substituted Indoles and Tryptophans. Part III. The Synthesis of the Four Bz-Cholo-indoles and -tryptophans," pp. 3499-3503 (1955).

Shvedov, V. I. et al., "Studies in the Enamine Field V. Synthesis of 1,2-Cyclohexanedione and 1,2-Cycloheptanedione Monoarylhydrazones and Transformations of These Compounds Under Conditions of the Fischer Reaction," *Journal of the Organic Chemistry of the USSR*, pp. 1586-1589.

Chemical Abstract, vol. 77, No. 5, Jul. 31, 1972, Columbus, Ohio, U.S.; Abstract No. 34327S, p. 504.

TRICYCLIC-CYCLIC AMINES AS NOVEL CHOLINESTERASE INHIBITORS

BACKGROUND OF THE INVENTION

This application is a continuation-in-part of U.S. Ser. No. 07/639,614, filed Jan. 10, 1991 now abandoned, which is a continuation-in-part of U.S. Ser. No. 07/476,928 filed Feb. 8, 1990 now abandoned.

The present invention relates to tricyclic-cyclic amines of the formula I below, and pharmaceutically acceptable salts of such compounds. The compounds of formula I are cholinesterase inhibitors and are useful in enhancing memory in patients suffering from dementia and Alzheimer's disease.

Alzheimer's disease is associated with degeneration of cholinergic neurons in the basal forebrain that play a fundamental role in cognitive functions, including memory. Becker et al., *Drug Development Research*, 12, 163-195 (1988). As a result of such degeneration, patients suffering from the disease exhibit a marked reduction in acetylcholine synthesis, choline acetyltransferase activity, acetylcholinesterase activity and choline uptake.

It is known that acetylcholinesterase inhibitors are effective in enhancing cholinergic activity and useful in improving the memory of Alzheimer's patients. By inhibiting acetylcholinesterase enzyme, these compounds increase the level of the neurotransmitter acetylcholine, in the brain and thus enhance memory. Becker et al., supra, report that behavioral changes following cholinesterase inhibition appear to coincide with predicted peak levels of acetylcholine in the brain. They also discuss the efficacy of the three known acetylcholinesterase inhibitors physostigmine, metrifonate, and tetrahydroaminoacridine.

SUMMARY OF THE INVENTION

The present invention relates to compounds of the formula

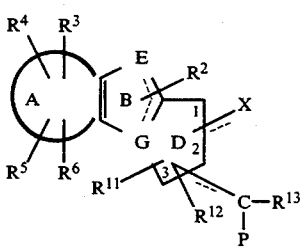

I wherein P is

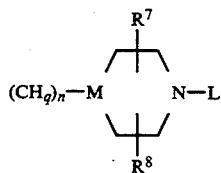

Ring A is benzo, thieno, pyrido, pyrazino, pyrimido, furano, selenolo or pyrrolo;

$R^2$ is hydrogen, (C-$C_4$)alkyl, benzyl, fluoro or cyano;

$R^3$, $R^4$, $R^5$ and $R^6$ are each independently selected from hydrogen, ($C_1$-$C_6$) alkoxy, benzyloxy, phenoxy, hydroxy, phenyl, benzyl, halo, nitro, cyano, $COOR^9$, $CONHR^9$, $NR^9R^{10}$, $NCOR^9COR^{10}$, ($C_1$-$C_6$) alkyl optionally substituted with from 1 to 3 fluorine atoms; $SO_pCH_2$-phenyl wherein p is 0, 1 or 2; pyridylmethyloxy or thienylmethyloxy; wherein the phenyl moieties of said phenoxy, benzyloxy, phenyl and benzyl groups, and the pyridyl and thienyl moieties of said pyridylmethyloxy and thienylmethyloxy may optionally be substituted with 1 or 2 substituents independently selected from halo, ($C_1$-$C_4$) alkyl, trifluoromethyl, ($C_1$-$C_4$)alkoxy, cyano, nitro and hydroxy;

or two of $R^2$, $R^3$, $R^4$, $R^5$ and $R^6$ are attached to adjacent carbon atoms and form, together with said adjacent carbon atoms, a saturated 5 or 6 membered ring wherein each atom of said ring is carbon, nitrogen or oxygen (e.g. a methylenedioxy or ethylenedioxy group or a lactam ring);

$R^9$ and $R^{10}$ are each independently selected from hydrogen and ($C_1$-$C_6$)alkyl, or $NR^9R^{10}$ together form a 4 to 8 membered ring wherein one atom of the ring is nitrogen and the others are carbon, oxygen or nitrogen, or $NR^9COR^{10}$ together form a 4 to 8 membered cyclic lactam ring;

G is carbon or nitrogen;

E is carbon, nitrogen, oxygen, sulfur, sulfoxide or sulfone;

the curved dashed line in ring B represents one double bond, so that ring B contains two double bonds, and the curved dashed line in ring D represents an optional double bond, so that ring D may contain 1 or 2 double bonds;

each of the straight dashed lines connecting, respectively, $R^{11}$ the carbon to which P is attached and X to ring D represents an optional double bond;

the carbon at any of positions 1-3 of ring D may optionally be replaced by nitrogen when such carbon is adjacent to a carbonyl group, the carbon atom of which is at position 1, 2 or 3 of ring D, so that ring D is a lactam ring;

X is O, S, $NOR^1$ hydrogen or ($C_1$-$C_6$)alkyl, with the proviso that X is double bonded to ring D only when the member of ring D to which it is bonded is carbon and X is O, S or $NOR^1$;

$R^1$ is hydrogen or ($C_1$-$C_6$)alkyl;

q is an integer from 1 to 2;

n is an integer from 1 to 3 when ring D is a lactam ring and n is an integer from 0 to 3 when ring D is not a lactam ring;

M is carbon or nitrogen;

L is phenyl, phenyl-($C_1$-$C_6$)alkyl, cinnamyl, or pyridylmethyl, wherein the phenyl moieties of said phenyl and phenyl -($C_1$-$C_6$)alkyl may optionally be substituted with 1-3 substituents independently selected from ($C_1$-$C_6$)alkyl, ($C_1$-$C_6$)alkoxy, ($C_1$-$C_4$)alkoxycarbonyl, ($C_1$-$C_4$)alkylcarbonyl or halo;

$R^{11}$ is hydrogen, halo, hydroxy, ($C_1$-$C_4$) alkyl, ($C_1$-$C_4$)alkoxy or oxygen;

$R^{12}$ and $R^{13}$ are each independently selected from hydrogen, fluoro, hydroxy, acetoxy, mesylate, tosylate, ($C_1$-$C_4$) alkyl, and ($C_1$-$C_4$)alkoxy; or $R^{12}$ and $R^{13}$ may, together with the atoms to which they are attached, when both of $R^{12}$ and $R^{13}$ are attached to carbon atoms, form a three, four or five membered ring wherein each atom of said ring is carbon or oxygen.

$R^7$ and $R^8$ are each independently selected from hydrogen, ($C_1$-$C_6$)alkyl, ($C_1$-$C_6$)alkoxy, wherein said ($C_1$–$C_6$)alkoxy is not attached to a carbon that is adjacent to a nitrogen; ($C_1$–$C_6$)alkoxycarbonyl, and ($C_1$–$C_6$)alkylcarbonyl;

or $R^8$ and $R^{12}$, together with the atoms to which they are attached, form a saturated carbocyclic ring containing 4 to 7 carbons wherein one of said carbon atoms may optionally be replaced with oxygen, nitrogen or sulfur;

with the proviso that:

(a) when E is carbon, nitrogen, oxygen, sulfur, sulfoxide or sulfone, then G is carbon;

(b) when G is nitrogen, then E is carbon or nitrogen;

(c) when either E and G are both nitrogen, or G is carbon and E is oxygen, sulfur, sulfoxide or sulfone, then $R^2$ is absent;

(d) each of the atoms at positions 1, 2 and 3 of ring D may be bonded by no more than one double bond; and (e) X is attached to the position on ring D that is adjacent to the position to which the hydrocarbon substituent containing P is attached.

The present invention also relates to the pharmaceutically acceptable acid addition salts of compounds of the formula I. Examples of such pharmaceutically acceptable acid addition salts are the salts of hydrochloric acid, p-toluenesulfonic acid, fumaric acid, citric acid, succinic acid, salicylic acid, oxalic acid, hydrobromic acid, phosphoric acid, methanesulfonic acid, tartaric acid, di-p-toluoyl tartaric acid, and mandelic acid.

This invention further relates to a pharmaceutically composition for inhibiting cholinesterase comprising a compound of the formula I or a pharmaceutically acceptable acid addition salt thereof, and a pharmaceutically acceptable carrier.

The invention further relates to a method for inhibiting cholinesterase in a mammal comprising administering to a mammal an amount of a compound of the formula I or a pharmaceutically acceptable acid addition salt thereof effective in inhibiting chlolinesterase.

The invention further relates to a method for enhancing memory or treating or preventing Alzheimer's disease in a mammal comprising administering to a mammal an amount of a compound of the formula I or a pharmaceutically acceptable acid addition or salt thereof effective in enhancing memory or treating or preventing Alzheimer's disease.

The term "mammal", as used herein, includes humans.

The term "halo", as used herein, includes chloro, bromo or fluoro.

The term "($C_1$–$C_4$) alkylcarbonyl" as used herein, refers to a substituent of the formula

wherein $R^{18}$ is ($C_1$–$C_4$) alkyl.

The term "phenylcarbonyl" as used herein, refers to a substituent of the formula V above, wherein is phenyl. The term "($C_1$–$C_4$) alkoxycarbonyl" refers to a substituent of the formula V above, wherein f is ($C_1$–$C_4$) alkoxy.

The term "($C_1$–$C_6$) alkoxycarbonyl" as used herein, refers to a substituent of the formula V above, wherein $R^7$ is ($C_1$–$C_6$) alkoxy.

The term "($C_1$–$C_4$)alkylcarbonyl", as used herein, refers to a substituent of the formula V above, wherein is ($C_1$–$C_6$)alkyl.

Preferred compounds of this invention are compounds of the formula I above, wherein E is carbon or nitrogen, G is nitrogen, ring A is benzo, pyrido or thieno, two of $R^3$, $R^4$ $R^5$ and $R^6$ are hydrogen and the other two are independently selected from hydrogen, methyl, ethyl, propyl, methoxy, ethoxy, propyloxy, benzyloxy, hydroxy, tosyloxy, fluoro, acetoxy, N-ethylcarbamate ester and N-methylcarbamate ester; X is oxygen or sulfur and is attached to the carbon at position "1" of ring D, each of $R^2$, $R^{11}$, $R^{12}$ and $R^{13}$ is hydrogen, the hydrocarbon chain to which P is attached is single or double bonded to ring D, and P is

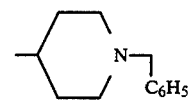

Other preferred compounds of this invention are those having formula I above, wherein E is carbon, nitrogen, sulfur or oxygen, G is carbon, ring A is benzo, pyrido or thieno, two of $R^3$, $R^4$, $R^5$ and $R^6$ are hydrogen and the other two are independently selected from hydrogen, methyl, ethyl, propyl, methoxy, ethoxy, propyloxy, benzyloxy, acetoxy, N-methylcarbamate ester, N-methylcarbamate ester, hydroxy, tosyloxy and fluoro, X is oxygen or sulfur and attached to the carbon at position "1" of ring D, each of $R^2$, $R^{11}$, $R^{12}$ and $R^{13}$ is hydrogen, the hydrocarbon chain to which P is attached is single or double bonded to ring D, and P is

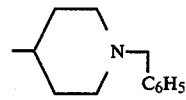

Specific preferred compounds of the invention are:

2,3-dihydro-2-[[1-(phenylmethyl)-4-piperidinyl]methylene]-1H-pyrrolo[1,2-a]indol-1-one;

2,3-dihydro-7-methoxy-2-[[1-(phenylmethyl)-4-piperidinyl]methylene]-1H-pyrrolo[1,2-a]indol-1-one;

2,3-dihydro-6,7-dimethoxy-2-[[1-(phenylmethyl)-4-piperidinyl]methylene]-1H-pyrrolo[1,2-a]indol-1-one;

2,3-dihydro-7-fluoro-2-[[1-(phenylmethyl)-4-piperidinyl]methylene]-1H-pyrrolo[1,2-a]indol-1-one;

2,3-dihydro-7-methyl-2-[[1-(phenylmethyl)-4-piperidinyl]methylene]-1H-pyrrolo[1,2-a]indol-1-one;

2,3-dihydro-6-methyl-2-[[1-(phenylmethyl)-4-piperidinyl]methylene]-1H-pyrrolo[1,2-a]indol-1-one;

2,3-dihydro-8-methyl-2-[[1-(phenylmethyl)-4-piperidinyl]methylene]-1H-pyrrolo[1,2-a]indol-1-one;

2,3-di hydro-6-methoxy-2-[[1-(phenylmethyl)-4-piperidinyl]methylene]-1H-pyrrolo[1,2-a]indol-1-one; 2,3-di hydro-7-benzyloxy-2-[[1-(phenylmethyl)-4-piperidinyl]methylene]-1H-pyrrolo[1,2-a]indol-1-one;

2,3-dihydro-7-ethoxy-2-[[1-(phenylmethyl)-4-piperidinyl]methylene]-1H-pyrrolo[1,2-a]indol-1-one;
2,3-dihydro-8-methoxy-2-[[1-(phenylmethyl)-4-piperidinyl]methylene]-1H-pyrrolo[1,2-a]indol-1-one;
2,3-dihydro-7-p-tosyloxy-2-[[1-(phenylmethyl)-4-piperidinyl]methylene]-1H-pyrrolo[1,2-a]indol-1-one;
2,3-dihydro-2-[[1-(phenylmethyl)-4-piperidinyl]methyl]-1H-pyrrolo[1,2-a]indol-1-one;
2,3-dihydro-7-methoxy-2-[[1-(phenylmethyl)-4-piperidinyl]methyl]-1H-pyrrolo[1,2-a]indol-1-one;
2,3-dihydro-7-fluoro-2-[[1-(phenylmethyl)-4-piperidinyl]methyl]-1H-pyrrolo[1,2-a]indol-1-one;
2,3-dihydro-6,7-dimethoxy-2-[[1-(phenylmethyl)-4-piperidinyl]methyl]-1H-pyrrolo[1,2-a]indol-1-one;
2,3-dihydro-9-methyl-2-[[1-(phenylmethyl)-4-piperidinyl]methyl]-1H-pyrrolo[1,2-a]indol-1-one;
2,3-dihydro-7-methyl-2-[[1-(phenylmethyl)-4-piperidinyl]methyl]-1H-pyrrolo[1,2-a]indol-1-one;
2,3-dihydro-6-methyl-2-[[1-(phenylmethyl)-4-piperidinyl]methyl]-1H-pyrrolo[1,2-a]indol-1-one;
2,3-dihydro-8-methyl-2-[[1-(phenylmethyl)-4-piperidinyl]methyl]-1H-pyrrolo[1,2-a]indol-1-one;
2,3-dihydro-6-methoxy-2-[[1-(phenylmethyl)-4-piperidinyl]methyl]-1H-pyrrolo[1,2-a]indol-1-one;
2,3-dihydro-6-benzyloxy-2-[[1-(phenylmethyl)-4-piperidinyl]methyl]-1H-pyrrolo[1,2-a]indol-1-one;
2,3-dihydro-7-ethoxy-2-[[1-(phenylmethyl)-4-piperidinyl]methyl]-1H-pyrrolo[1,2-a]indol-1-one;
2,3-dihydro-8-methoxy-2-[[1-(phenylmethyl)-4-piperidinyl]methyl]-1H-pyrrolo[1,2-a]indol-1-one;
2,3-dihydro-7-tosyloxy-2-[[1-(phenylmethyl)-4-piperidinyl]methyl]-1H-pyrrolo[1,2-a]indol-1-one;
2,3-dihydro-7-hydroxy-2-[[1-(phenylmethyl)-4-piperidinyl]methyl]-1H-pyrrolo[1,2-a]indol-1-one;
2,3-dihydro-2-methyl-7-methoxy-2-[[1-(phenylmethyl)-4-piperidinyl]methyl]-1H-pyrrolo[1,2-a]indol-1-one;
2,3-dihydro-7-acetoxy-2-[[1-(phenylmethyl)-4-piperidinyl]methyl]-1H-pyrrolo[1,2-a]indol-1-one;
2,3-dihydro-1-oxo-2-[[1-(phenylmethyl)-4-piperidinyl]methyl]-1H-pyrrolo[1,2-a]indole-7-ol, methyl carbamate ester;
2,3-dihydro-7-methoxy-2-[[1-(phenylmethyl)-4-piperidinyl]methyl]-1H-pyrrolo[1,2-a]indol-1-thione;
2,3-dihydro-7-methyl-2-[[1-(phenylmethyl)-4-piperidinyl]methyl]-1H-pyrrolo[1,2-a]indol-1-thione;
2,3-dihydro-7-hydroxy-2-[[1-(phenylmethyl)-4-piperidinyl]methyl]-1H-pyrrolo[1,2-a]indol-1-thione;
1,2,3,4-tetrahydro-2-[[1-(phenylmethyl)-4-piperidinyl]methyl]-cyclopent[b]indol-1-one;
1,2,3,4-tetrahydro-2-[[1-(phenylmethyl)-4-piperidinyl]methylene]-cyclopent[b]indol-3-one;
1,2,3,4-tetrahydro-4-methyl-2-[[1-(phenylmethyl)-4-piperidinyl]methylene]-cyclopent[b]indol-3-one;
1,2,3,4-tetrahydro-5-methoxy-2-[[1-(phenylmethyl)-4-piperidinyl]methylene]-cyclopent[b]indol-3-one;
1,2,3,4-tetrahydro-6-methoxy-2-[[1-(phenylmethyl)-4-piperidinyl methylene]-cyclopent[b]indol-3-one;
1,2,3,4-tetrahydro-8-methoxy-2-[[1-(phenylmethyl)-4-piperidinyl methylene]-cyclopent[b]indol-3-one;
1,2,3,4-tetrahydro-7-methoxy-2-[[1-(phenylmethyl)-4-piperidinyl methylene]-cyclopent[b]indol-3-one;
1,2,3,4-tetrahydro-4-benzoyl-2-[[1-(phenylmethyl)-4-piperidinyl]methylene]-cyclopent[b]indol-3-one;
1,2,3,4-tetrahydro-6,7-dimethoxy-2-[[1-(phenylmethyl)-4-piperidinyl]methylene]-cyclopent[b]indol-3-one;
1,2,3,4-tetrahydro-6,7-dimethyl-2-[[1-(phenylmethyl)-4-piperidinyl]methylene]-cyclopent[b]indol-3-one;
1,2,3,4-tetrahydro-2-[[1-(phenylmethyl)-4-piperidinyl]methyl]-cyclopent[b]indol-3-one;
1,2,3,4-tetrahydro-4-methyl-2-[[1-(phenylmethyl)-4-piperidinyl]methyl]-cyclopent[b]indol-3-one;
1,2,3,4-tetrahydro-5-methoxy-2-[[1-(phenylmethyl)-4 piperidinyl]methyl]-cyclopent [b]indol-3-one;
1,2,3,4-tetrahydro - 6 -methoxy- 2 -[[1-(phenylmethyl)-4-piperidinyl]methyl]-cyclopent [b]indo 1-3-one;
1,2,3,4-tetrahydro-8-methoxy-2-[[1-(phenylmethyl)-4-piperidinyl]methyl]-cyclopent[b]indol-3-one;
1,2,3,4-tetrahydro-4-benzyl-2-[[1-(phenylmethyl)-4-piperidinyl]methyl]-cyclopent[b]indol-3-one;
1,2,3,4-tetrahydro-7-methoxy-2-[[1-(phenylmethyl)-4-piperidinyl]methyl]-cyclopent[b]indol-3-one;
1,2,3,4-tetrahydro-4-benzoyl-2-[[1-(phenylmethyl)-4-piperidinyl]methyl]-cyclopent[b]indol-3 -one;
1,2,3,4-tetrahydro-4-tosyl-2-[[1-(phenylmethyl)-4-piperidinyl]methyl]-cyclopent[b]indol-3 -one;
1,2,3,4-tetrahydro-6,7-dimethoxy-2-[[1-(phenylmethyl)-4-piperidinyl]methyl]-cyclopent[b]indol-3 -one;
1,2,3,4-tetrahydro-6-hydroxy-2-[[1-(phenylmethyl)-4 piperidinyl]methyl]-cyclopent[b]indol-3-one;
1,2,3,4-tetrahydro-7-hydroxy-2-[[1-(phenylmethyl)-4-piperidinyl]methyl]-cyclopent[b]indol-3-one;
1,2,3,4-tetrahydro-6,7-dimethyl-2-[[1-(phenylmethyl)-4-piperidinyl]methyl]-cyclopent[b]indol-3-one;
1,2,3,4-tetrahydro-4-methyl-2-[[1-(phenylmethyl)-4-piperidinyl]methyl]-cyclopent[b]indol-3-thione;
1,2,3,4-tetrahydro-5-methoxy-2-[[1-(phenylmethyl)-4-piperidinyl]methyl]-cyclopent[b]indol-3-thione;
1,2,3,4-tetrahydro-6-methoxy-2-[[1-(phenylmethyl)-4-piperidinyl]methyl]-cyclopent[b]indol-3-thione;
1,2,3,4-tetrahydro-8-methoxy-2-[[1-(phenylmethyl)-4-piperidinyl]methyl]-cyclopent[b]indol-3-thione;
1,2,3,4-tetrahydro-7-methoxy-2-[[1-(phenylmethyl)-4-piperidinyl]methyl]-cyclopent[b]indol-3 -thione;
1,2,3,4-tetrahydro-6,7-methoxy-2-[[1-(phenylmethyl)-4-piperidinyl]methyl]-cyclopent[b]indol-3 -thione;
1,2,3,4-tetrahydro-6-hydroxy-2-[[1-(phenylmethyl)-4-piperidinyl]methyl]-cyclopent[b]indol-3 -thione;
1,2,3,4-tetrahydro-7-hydroxy-2-[[1-(phenylmethyl)-4-piperidinyl]methyl]-cyclopent[b]indol-3 -thione;
1,2,3,4-tetrahydro-6,7-dimethyl-2-[[1-(phenylmethyl)-4-piperidinyl]methyl]-cyclopent[b]indol-3-thione;
2,3-dihydro-6-methoxy-2-[[1-(phenylmethyl)-4-piperidinyl]methylene]-1H-cyclopent[b](benzo[b]furan)-1-one;
2,3-dihydro-6-methoxy-2-[[1-(phenylmethyl)-4-piperidinyl]methyl]-1H-cyclopent[b](benzo [b]furan)-1-one;
2,3-dihydro-2-[[1-(phenylmethyl)-4-piperidinyl]methyl]-1H-pyrrolo[1,2-a]benzimidazol-1-one;
2,3-dihydro-6-methoxy-2-[[1-(phenylmethyl)-4-piperidinyl]]methylene]-1H-cyclopent[b](benzo[b]thieno)-1one;

6,7-dihydro-6-[[1-(phenylmethyl)-4-piperidinyl]methyl]-5H-thieno [3,2-b]-pyrrolizine-5-one;

2,3-dihydro-2 -[[1-(phenylmethyl)-4-piperidinyl]methyl]-1H-pyrrolo[1,2-a](thieno[2,3-b]pyrrol)-1-one;

2,3-dihydro-7-methoxy-2-[[1-(phenylmethyl)-4-piperidinyl]methylene]-1H-pyrrolo[1,2-a](6-azaindol )-1-one;

2,3-dihydro-7-methoxy-2-[[1-(phenylmethyl)-4-piperidinyl]methyl]-1H-pyrrolo[1,2-a](6-azaindol )-1-one;

1,2,3,4-tetrahydro-6-methoxy-2-[[1-(phenylmethyl)-4-piperidinyl]ethyl]-pyrrolo[3,4-b]indol-3-one;

1,2,3,4-tetrahydro-6-methyl-2-[[1-(phenylmethyl)-4-piperidinyl]ethyl]-pyrrolo[3,4-b]indol-3-one;

1,2,3,4-tetrahydro-7-methyl-2-[2-[1-(phenylmethyl)-4-piperidinyl]ethyl]-pyrrolo[3,4-b]indol-3-one;

2,3-dihydro-1-hydroxy-7-methoxy-2-[[1-(phenylmethyl)-4-piperidinyl]methylene]-1H-pyrrolo[1,2-a]indole;

2,3-dihydro-1-hydroxy-7-methoxy-2-[[1-(phenylmethyl)-4-piperidinyl]methyl]-1H-pyrrolo[1,2-a]indole;

2,3-dihydro-1-acetoxy-7-methoxy-2-[[1-(phenylmethyl)-4-piperidinyl]methyl]-1H-pyrrolo[1,2-a]indole;

2,3-dihydro-7-methoxy-2-[[1-(phenylmethyl)-4-piperidinyl]methyl]-1H-pyrrolo[1,2-a]indol-1-oxime;

1,4-dihydro-7-chloro-2-[2-[1-(phenylmethyl)-4-piperidinyl]ethyl]pyrrolo[3,4-b]indol-3(2H)-one;

1,2-dihydro-7-methyl-2-[2-[1-(phenylmethyl)-4-piperidinyl]ethyl]pyrrolo[3,4-(benzo[b]thieno)-1H-3-one;

1,2-dihydro-6-methyl-2-[2-[1-(phenylmethyl)-4-piperidinyl]ethyl]pyrrolo[3,4-b](benzo[b]thieno) 1H-3-one;

1,2-dihydro-7-chloro-2-[2-[1-(phenylmethyl)-4-piperidinyl]ethyl]pyrrolo[3,4-b](benzo[b]thieno)1H-3-one;

2,3-dihydro-5-methyl-2-[[1-(phenylmethyl)-4-piperidinyl]methylene]-1H-cyclopent[b](benzo[b]thieno)-1-one;

2,3-dihydro-5-methyl-2-[[1-(phenylmethyl)-4-piperidinyl]methyl]-1H-cyclopent[b](benzo[b]thieno)-1-one;

The compounds of formula I may have optical centers and may therefore occur in different isomeric forms. The invention includes all isomers of such compounds of formula I, including mixtures thereof.

DETAILED DESCRIPTION OF THE INVENTION

The preparation of compounds having the formula I and certain of the starting materials used in their synthesis is illustrated in the following reaction schemes. In the reaction schemes and discussion that follow, the compounds of formula I are represented by the formulae I-A, I-B, I-C. . . Except where otherwise stated in the reaction schemes and discussion that follow, $R^1$, $R^2$, $R^3$, $R^4$, $R^5$, $R^6$, $R^7$, $R^8$, $R^9$, $R^{10}$, $R^{11}$, $R^{12}$, $R^{13}$, A, B, D, E, G, P, n, q, p, M, N, L, and the curved and straight dashed lines are defined as above.

All articles, books, patents and patent applications cited in the following discussion are incorporated herein by reference.

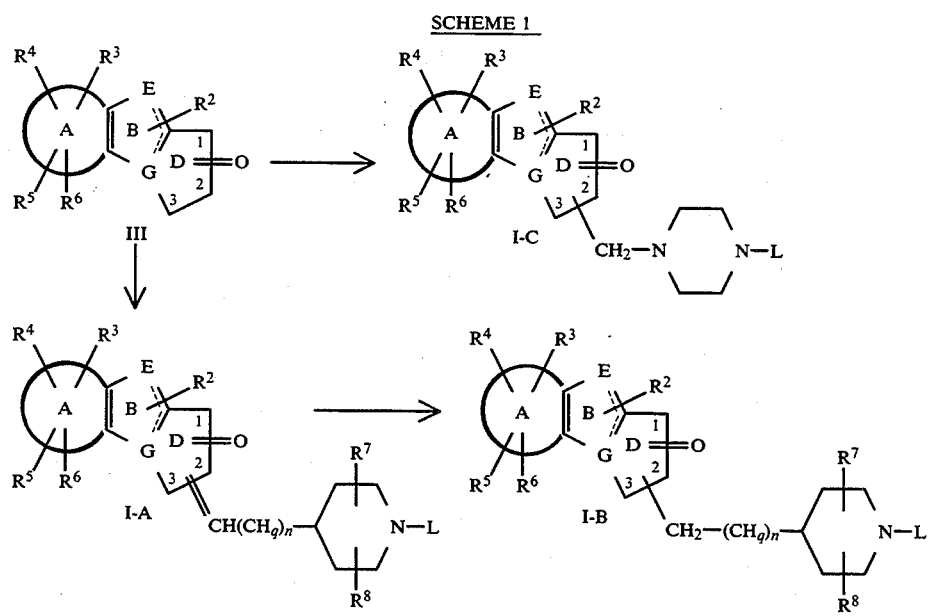

SCHEME 1

SCHEME 2
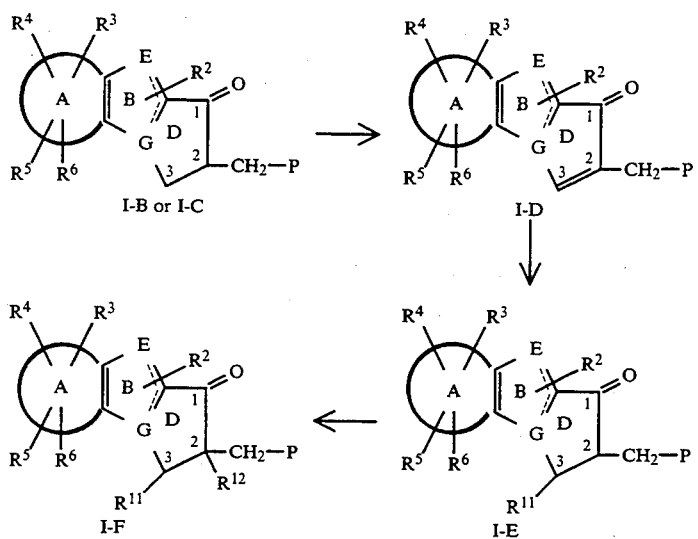
SCHEME 3
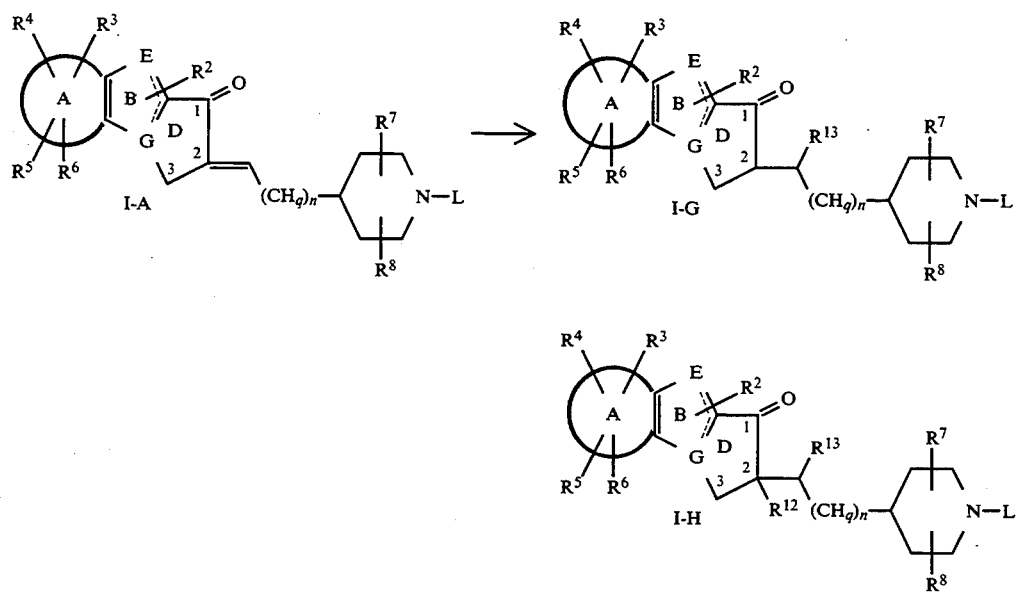
SCHEME 4
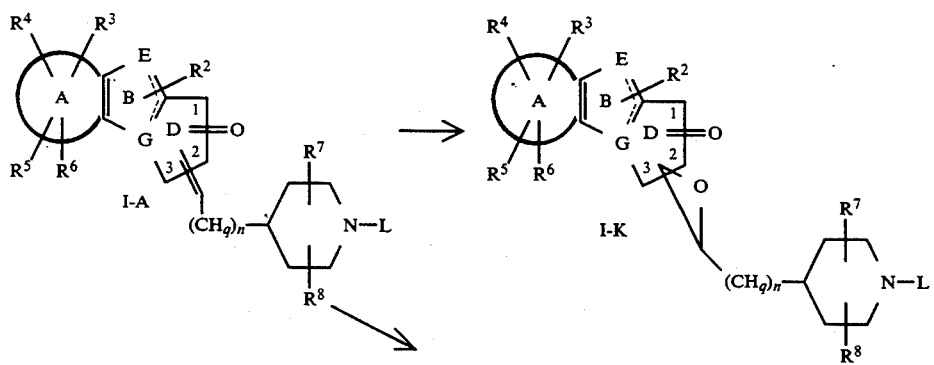

SCHEME 4
-continued
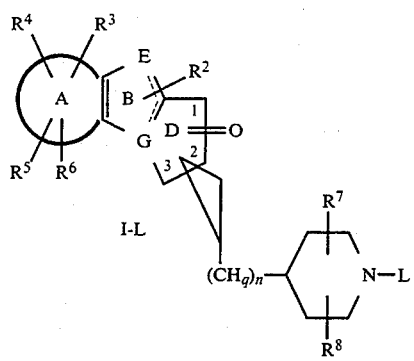
SCHEME 5
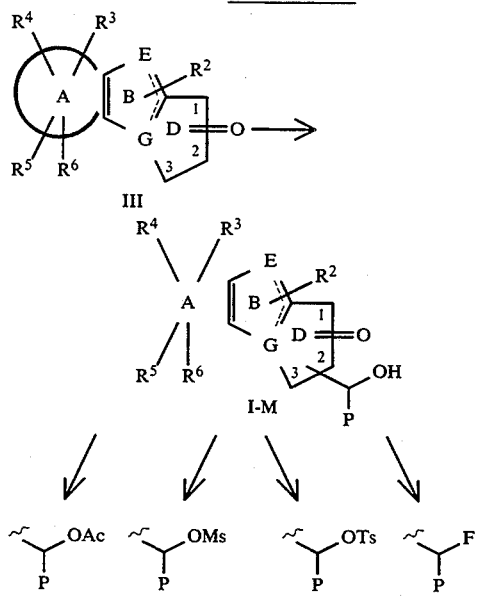
SCHEME 6
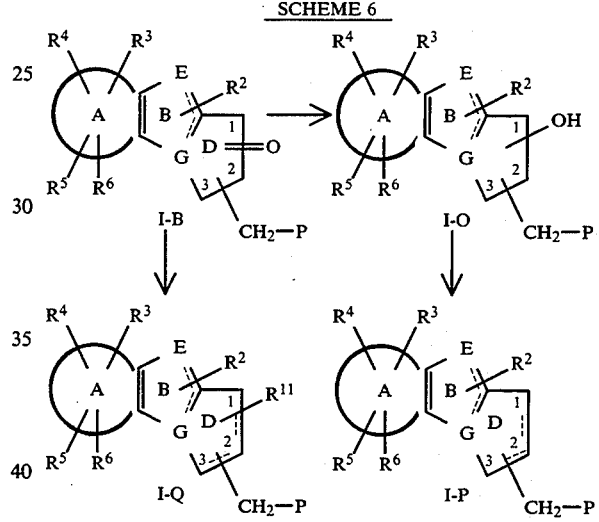
SCHEME 7
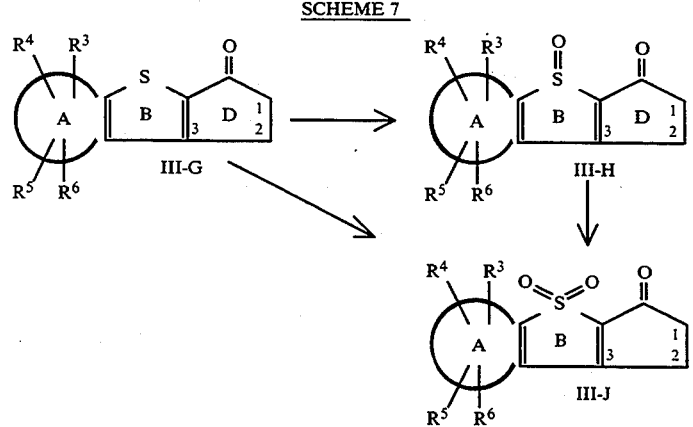

SCHEME 8

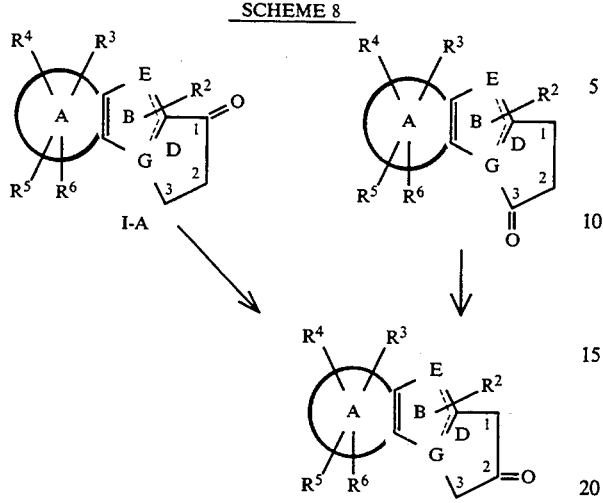

SCHEME 9

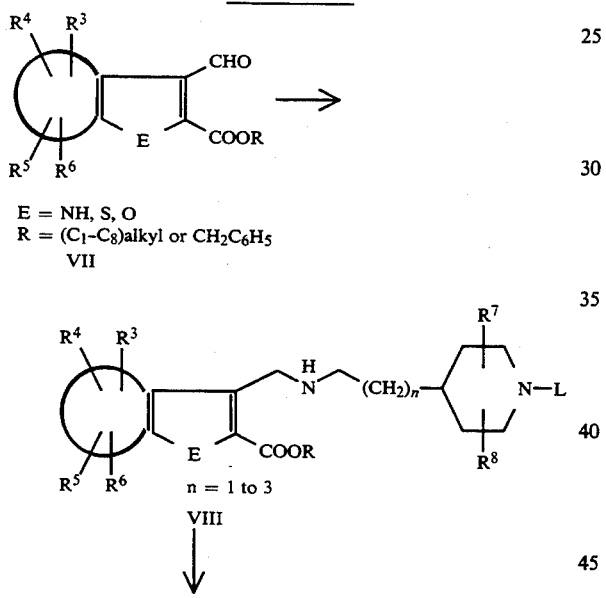

E = NH, S, O
R = (C$_1$-C$_8$)alkyl or CH$_2$C$_6$H$_5$
VII

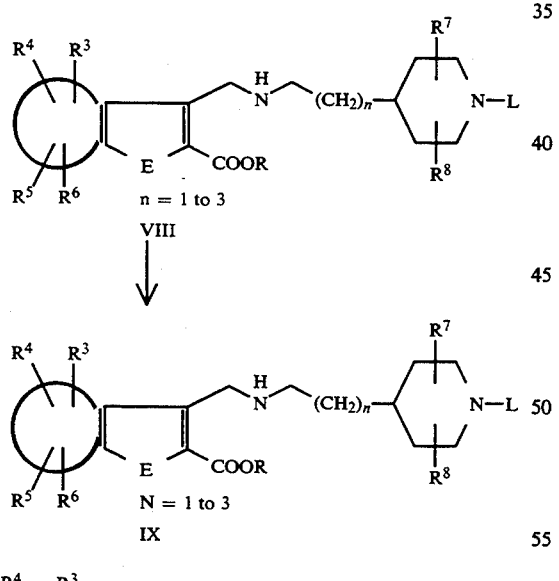

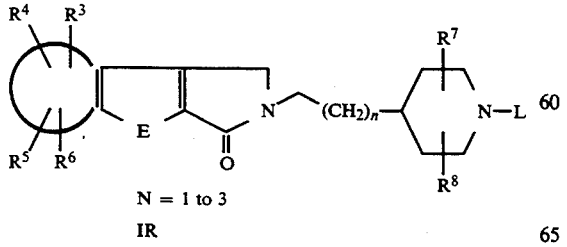

The novel compounds of formula I are prepared from a variety of tricyclic ketones having the formula

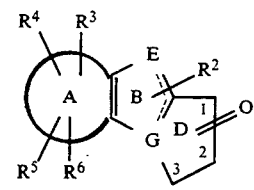

III

Listed below are several species of the tricyclic ketones of formula III, represented, respectively, by the formulae III-A through III-M, followed by the methods by which they may be obtained.

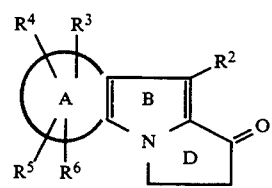

III-A

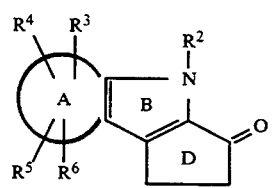

III-B

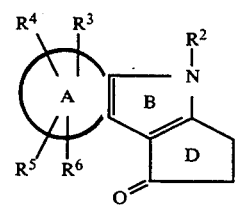

III-C

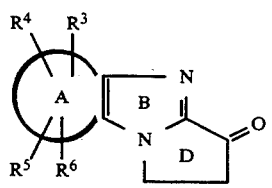

III-D

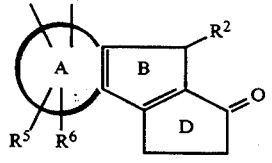

III-E

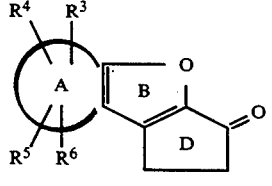

III-F

III-G

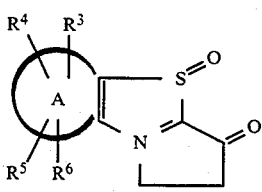
III-H

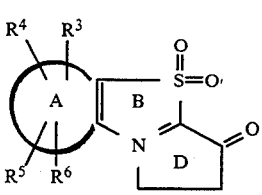
III-J

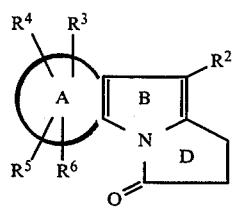
III-K

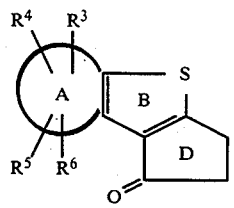
III-L

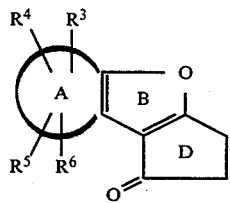
III-M

Tricyclic ketones having the formula III-A may be prepared from compounds of the formula

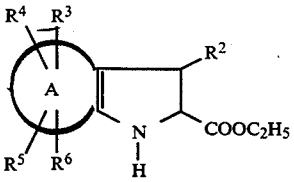
VI by known methods described in the literature.

Compounds of the formula VI, wherein ring A is benzo may be prepared by the Fischer-Indole Synthesis (J. Chem. Soc. 7185 (1965); J. Chem. Soc., 3499 (1955); J. Chem. Soc. Trans. 59, 209 (1891); Brian Robinson, The Fischer Indole Synthesis (1982)) and by the Reissert Synthesis (Heterocyclic Compounds, 3, 18 (1962); J. Am. Chem. Soc., 71, 761 (1949)). Compounds of the formula VI, wherein ring A is pyrido, pyrazino or pyrimido, may be prepared by a method analogous to the Reissert Synthesis (J. Med. Chem., 2, 1272 (1989); J. Am. Chem. Soc., 87, 3530 (1965)). Compounds of the formula VI, wherein ring A is benzo, thieno, furano, selenolo or pyrrolo, may be prepared as described in Collect. Czech. Chem. Commun., 46, 2564 (1981), (Can. J. Chem., 56, 1429 (1978) and J. Chem. Soc. Perkin Trans. I, 931 (1987).

The tricyclic ketones of the formula III-A may be synthesized from the corresponding compounds of the formula VI, according to a procedure analogous to that described in J. Med. Chem., 28, 921 (1985). Those compounds of the formula III-A wherein $R^2$ is other than hydrogen may also be synthesized from the corresponding compounds of the formula VI, according to a procedure analogous to that described in Arch. Pharm., 308, 779 (1975).

Tricyclic ketones of the formula III-B wherein ring A is benzo may be prepared from the corresponding compounds having the formula

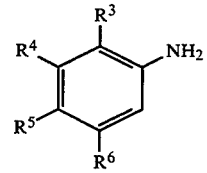
III-K using the Fischer-Indole Synthesis, as described in Heterocycles, 12, 913 (1979), Khim-Farm Zh, USSR, 23, 229 (1989), J. Org. Chem., USSR (English), 1586 (1966) and Japanese Patent 56083471. Compounds of the formula III-B, wherein ring A is benzo, thieno, pyrido, pyrazino, pyrimido, furano, selenolo or pyrrolo may be prepared from the corresponding compounds having the formula

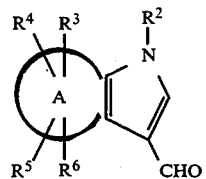
III-L by a method analogous to that described in J. Med. Chem., 32, 1098 (1989). Alternatively, they may be prepared starting with corresponding compounds of the formula

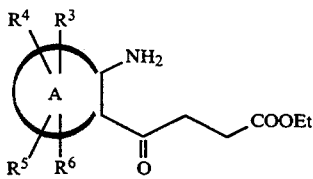

by a procedure analogous to that described in Bull. Chem. Soc. Japan, 49, 737 (1976) and Am. Chem., 662, 147 (1963).

Tricyclic ketones having the formula III-C, may be prepared according to the methods described in J. Org. Chem., 42, 1213 (1977), J. Heterocyclic Chem. 24, 1321, (1987); J. Chem. Soc., 700 (1951), Ann. Chem., 696, 116 (1966), and J. Org. Chem., 45, 2938 (1980). Tricyclic ketones having the formula III-D, may be obtained as follows. First, a compound having the formula

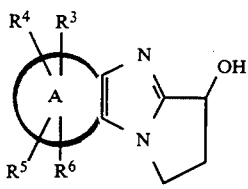

is synthesized from the corresponding compound of the formula

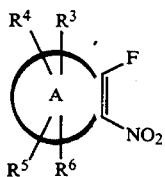

by a procedure analogous to that described in *J. Chem. Soc., C* 1, 70 (1969). The alcohol product is then oxidized to form the desired tricyclic ketone. The oxidation reaction is generally performed using manganese dioxide or selenium dioxide in a solvent such as methylene chloride, benzene, chloroform, toluene, dioxane or tetrahydrofuran (THF) at a temperature from about room temperature to about the reflux temperature of the solvent.

Tricyclic ketones having the formula III-E may be prepared from the corresponding compounds having the formula

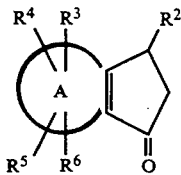

by a method analogous to that described in *J. Chem. Soc.*, 863 (1951) and *J. Org. Chem.*, 29, 175 (1964).

Tricyclic ketones of the formulae III-F and III-G may be prepared from the corresponding compounds of the formula

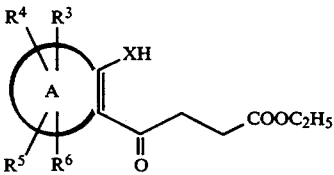

according to a procedure analogous to that described in *Bull. Chem. Soc.*, Japan, 49, 737 (1976), Ann. Chem., 662, 147 (1963) and *J. Heterocyclic Chem.*, 7, 107 (1970).

Tricyclic ketones having the formula III-H may be prepared from the corresponding tricyclic ketones of the formula III-G as illustrated in scheme 7. The appropriate compound of the formula III-G is reacted with one equivalent of a peracid such as m-chloroperbenzoic acid or peracetic acid, in a suitable reaction inert solvent such as chloroform or methylene chloride, at a temperature from about 0° to about 70° C., to yield the desired product of formula III-H. Alternatively, the appropriate compound of the formula III-G can be reacted with sodium periodate in a water/alcohol solvent such as water/methanol or water/ethanol at a temperature from about 0° to about 70° C.

The preparation of tricyclic ketones having the formula III-J is also illustrated in scheme 7. These compounds may be obtained starting with the corresponding compounds of the formula III-G or those of the formula III-H. The first method involves reacting the appropriate compound of the formula III-G with potassium permanganate in a suitable reaction inert solvent such as acetone/water, at a temperature from about 0° to about 50° C. Alternatively, the appropriate compound of the formula III-G may be reacted with greater than two equivalents of m-chloroperbenzoic acid or peracetic acid in a suitable reaction inert solvent such as chloroform or methylene chloride, at a temperature from about 0° to about 60° C. Such appropriate compound of the formula III-G may also, alternatively, be reacted with hydrogen peroxide in a water/alcohol solvent such as water/methanol or water/ethanol, at a temperature from about 0° to about 50° C. All three of the foregoing reactions yield tricyclic ketones of the formula III-H.

As mentioned above, tricyclic ketones of the formula III-J may also be prepared from the corresponding compounds of the formula III-H. Such compounds of the formula III-H will yield the desired tricyclic ketones of the formula III-H when reacted with either a peracid or hydrogen peroxide. Each of these reactions is typically carried out as described in the preceding paragraph.

Tricyclic ketones of the formula III-K may be prepared by a procedure analogous to those described in *Ann. Chem.*, 1437 (1985), *Ann. Chem.*, 1422 (1985); *Ann. Chem.*, 239 (1989); Zimmer, H., *Natural Product Gordon Research Conference, New Hampton School* (July, 1989).

Tricyclic ketones of the formulae III-L and III-M may be prepared by a method analogous to that described in European Patent Application EP 317088.

Scheme 8 illustrates how tricyclic ketone intermediates containing a carbonyl group at position "2" of ring D (i.e., wherein an oxygen is double bonded to the carbon at position "2") may be obtained from the corresponding tricyclic ketones wherein the carbonyl group is at position "1" or "3" of ring D. This procedure is analogous to that described in *Can. J. Chem.*, 60, 2678 (1982).

The novel compounds of formula I are prepared from tricyclic ketones of the formula III as illustrated in Schemes 1–6 and described below.

Referring to scheme 1, compounds of the formula I-A may be prepared by reacting a tricyclic ketone of the formula III with an aldehyde of the formula

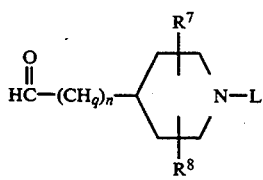

This reaction is generally carried out in a suitable reaction inert solvent in the presence of a base. Sodium hydride, piperidine or pyrrolidine may be used as the base, and the reaction conducted in a solvent such as tetrahydrofuran (THF), dimethylformamide (DMF), dioxane or toluene, with or without ethanol, at a temperature from about −40° to about 110° C. Alternatively, lithium or sodium diisopropylamide or lithium or sodium bis(trimethylsilyl)amide may be used as the base. When using such alternative method, the base is typically first added to the compound of formula III in a solvent such as THF, methylene chloride or toluene, preferably THF, at a temperature from about −°78 to about 0° C., followed by addition of the aldehyde. After addition of the aldehyde, the reaction mixture is stirred at a temperature from about −78° to about 40° C., preferably from about 0° C. to about room temperature. In a second alternative method, a sodium or potassium ($C_1$–$C_4$) alkoxide may be used as the base, and the reaction conducted in a reaction inert solvent such as toluene, DMF, THF or methylene chloride, with or without ethanol (1 to 3 equivalents to base), or in a lower alcohol, at a temperature from about −40° C. to about the reflux temperature of the solvent preferably from about 0° C. to about room temperature.

Preferably, the foregoing reaction of the tricyclic ketone and aldehyde is carried out using sodium hydride, piperidine, pyrrolidine or lithium diisopropyl amide as the base and THF or toluene as the solvent, at a temperature from about 0° C. to about 110° C. The foregoing reaction, using any of the three above methods, may be quenched with 1–3 equivalents of acetyl chloride, mesyl chloride or tosyl chloride, to give the desired compound of formula I-A.

Compounds of the formula I-B may be prepared by hydrogenating the corresponding compound of formula I-A. The hydrogenation is usually carried out using platinum dioxide or palladium on charcoal, in a suitable reaction inert solvent, at a temperature from about 15° to about 70° C. and a pressure from about 0.5 to 6 atm. Examples of suitable solvents are lower alcohols, ethyl acetate and THF, with or without ethanol. The preferred solvent is a mixture of ethanol and THF or a mixture of ethanol and ethyl acetate, and the preferred temperature is about room temperature.

Formula IC, also shown in scheme 1, represents compounds wherein P is

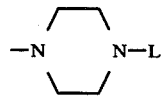

Compounds of the formula IC may be obtained, as illustrated in scheme 1, from tricyclic ketones of the formula III by reacting said tricyclic ketone with formaldehyde or a formaldehyde polymer and a compound of the formula

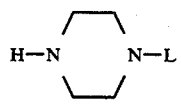

Generally, this reaction is conducted in a suitable reaction inert solvent such as a lower alcohol/water mixture or THF, and at a temperature from about 10° C. to about 200° C. Preferably, the solvent is alcohol/water, the temperature is from about room temperature to about 100° C. and the pH of the reaction mixture is from about 2.5 to about 3.5.

Compounds of the formula I-B or I-C may be converted to the corresponding compounds of the formula I-D, I-E and I-F, by the procedure illustrated in scheme 2. Compounds of the formula I-B may be converted to the corresponding compounds of the formula I-D by the following two methods. The first method involves brominating a compound of the formula IB or IC and then subjecting the resulting brominated compound to an elimination reaction. The bromination step is typically carried out by reacting the compound of formula I-B with a brominating agent such as liquid bromine, pyridinium bromide perbromide or N-bromosuccinimide, in the presence of a catalytic amount of benzoyl peroxide, in a suitable reaction inert solvent. Examples of suitable solvents are carbon tetrachloride, methylene chloride and THF. Carbon tetrachloride is preferred. Reaction temperatures may range from about 0° to about 80° C., with about 80° C. being preferred. The elimination reaction is typically carried out by reacting the resulting brominated compound from the previous step with a base such as diazabicycloundecane (DBU) or diazabicyclononane (DBN). Suitable solvents for this reaction include THF, methylene chloride, and chloroform, with methylene chloride being preferred. Suitable temperatures range from about 0° to about 100° C., with about 70° C. being preferred.

The second method involves adding selenium to a compound of the formula I-B and then subjecting the resulting selenium derivative to an elimination reaction. The selenium addition is typically carried out by reacting a compound of the formula I-B with a selenium agent such as phenylselenium chloride,

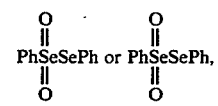

in a suitable reaction inert solvent in the presence of a base. Examples of bases that may be used are sodium hydride, lithium diisopropylamide or sodium or potassium ($C_1$–$C_4$) alkoxides. Examples of suitable solvents are THF, methylene chloride and toluene. THF is preferred. The reaction may be conducted at temperatures from about −78° C. to about room temperature. The elimination reaction is typically carried out by reacting the resulting selenium derivative from the previous step with an oxidizing agent such as sodium periodate. Suitable solvents for this reaction include water/lower alcohol mixtures, dioxane and THF, with ethanol/water being preferred. Reaction temperatures may range from about 0° to about 150° C. Temperatures from about 0° C. to about room temperature are preferred.

The $R^{11}$ substituent may be added to ring D of the compounds of formula I as illustrated by the conversion of compounds of the formula I-D to the corresponding compounds of the formula I-E, shown in scheme 2. This is accomplished by reacting the appropriate compound of the formula I-D with a compound of the formula (R)2 CuLi, in a suitable reaction solvent, at a temperature from about −78 to about 50° C. Examples of suitable solvents include THF, methylene chloride, dioxane, and ether. THF is the preferred solvent. The reaction may optionally be conducted in the presence of a compound having the formula $(R^{15})_3SiCl$, wherein $R^{15}$ is methyl or ethyl.

The $R^{12}$ substituent may be added to ring D of the compounds of the formula I, as illustrated by the conversion of compounds of the formula I-E to compounds of the formula I-F, also shown in scheme 2. This is accomplished by reacting the appropriate compound of the formula I-D with a base in a suitable reaction insert solvent, and then adding a compound of the formula $R^{16}X$, wherein X is a leaving group, to the reaction mixture. Generally, this reaction is conducted at a temperature from about $-78$ to about 40° C., and preferably from about 0° C. to about room temperature. Bases that may be used include sodium hydride, lithium diisopropylamide, triethylamine, and sodium and potassium $(C_1-C_4)$ alkoxides. The preferred bases are lithium diisopropylamide and sodium hydride. Suitable solvents include THF, methylene chloride, toluene, ether and DMF. The preferred solvent is THF. Suitable leaving groups include iodine, bromine, rosylate and mesylate.

Compounds of the formula I that are identical, respectively, to those of formulae I-D, I-E and I-F, except that the carbonyl group is at position "2" or position "3" of ring D rather than position "1" of ring D, may be prepared by the methods described above and illustrated in scheme 2, substituting the starting compounds of, respectively, formulae I-C, I-D and I-E with the corresponding compounds wherein the carbonyl group is at position "3" of ring D.

Scheme 3 illustrates the preparation of the novel compounds of the invention having the formulae I-G and I-H from compounds of the formula I-A. The conversion of compounds of the formula I-A to the corresponding compounds of the formula I-G illustrates the addition of the $R^{13}$ substituent to ring D. This is accomplished by reacting the appropriate compound of the formula I-A with a compound of the formula $(R^{13})_2CuLi$, in a suitable solvent at a temperature from about $-78°$ to about 40° C. Examples of suitable solvents include THF, methylene chloride, dioxane and ether. THF is the preferred solvent. The reaction may optionally be conducted in the presence of a compound having the formula $(R^{15})_3SiCl$, wherein $R^{15}$ is methyl or ethyl.

Compounds of the formula I-H may be prepared from the corresponding compounds of the formula I-G by addition of the $R^{12}$ substituent to the carbon at position "2" of ring D, according to the method described above from preparing compounds of the formula I-E from the corresponding compounds of the formula I-D.

Compounds identical to those of formulae I-G and I-H, except that the carbonyl group is at position "3" of ring D, may be prepared from the corresponding compounds identical to compounds of formulae I-A and I-G, except that the carbonyl group is at position "2" or position "3" of ring D, respectively, according to the methods described above for preparing compounds of the formulae I-G and I-H.

Scheme 4 illustrates a method of synthesizing of compounds of the formulae I-K and I-L from the corresponding compounds of the formula I-A. To obtain compounds of the formula I-K, the corresponding compounds of the formula I-A are reacted with an epoxidizing agent. An example of a suitable epoxidizing agent is sodium hydroxide/hydrogen peroxide. This reaction is usually conducted in a reaction inert solvent such as a mixture of water and a lower alcohol, preferably water-/ethanol. The reaction temperature may range from about $-20°$ to about 70° C., with about room temperature being preferred.

Compounds of the formula I-L may be obtained from the corresponding compounds of the formula I-A, via a Simmons-Smith reaction (See *J. Org. Chem.*, 54, 5994 (1989) and J. Org. Chem., 52, 3943 (1987). This reaction is carried out by reacting a derivative of the formula I-A with methylene iodide/zinc copper amalgam. Typically, this reaction is carried out at a temperature from about 0° to about 150° C., preferably from about 0° C. to about room temperature. Suitable solvents include ether, dimethoxyethane and THF. Dimethoxyethane is the preferred solvent.

Compounds of the formula I-M may be obtained as illustrated in scheme 5. First, a tricyclic ketone of the formula III is reacted with a $(C_1-C_4)$alkyl silyl chloride or a Lewis acid, in the presence of a base. Examples of appropriate Lewis acids are $(R^{17})_2AlCl$ or $(R^{17})_2BCl$, wherein $R^{17}$ is $(C_1-C_4)$ alkyl or cyclohexyl. Appropriate bases include triethylamine and diisopropylethylamine. The reaction is generally conducted at a temperature from about $-78°$ C. to about 50° C., preferably form about $-78°$ C. to about room temperature. Suitable solvents include THF, methylene chloride, toluene, ether or dioxane. The preferred solvent is THF Then, a compound of the formula

is added to the reaction mixture, with or titanium tetrachloride.

Derivatives of compounds of the formula I-M, wherein the hydroxy group is replaced by either acetate, mesylate, tosylate or fluoro, may be prepared as follows. To obtain an acetate derivative, the corresponding compound of the formula I-M is reacted with acetic anhydride or acetyl chloride. This reaction is generally conducted in the presence of a base such as triethylamine, diisopropylethylamine or pyridine, and at a temperature from about 0° to about 60° C., preferably from about 10° to about 30° C. Suitable solvents include methylene chloride, chloroform and THF, with methylenechloride being preferred. The mesylate and tosylate derivatives may be obtained using the same method and substituting respectively, mesyl chloride or tosyl chloride for acetic anhydride or acetyl chloride.

Fluoro derivatives may be prepared by reacting the corresponding compound of the formula I-M with diethylaminosulfonium trifluoride. Typically this reaction is carried out at a temperature from about $-78°$ C. to about room temperature, in an appropriate reaction inert solvent such as methylene chloride, THF or ether. The preferred temperature is from about $-78°$ to 0° C. and the preferred solvent is THF.

Compounds identical to those having the formula IA or IB except that the carbonyl group in ring D is replaced by $C=NOR^1$ may be prepared by reacting the corresponding compounds of formula I-A or I-B with a compound of the formula $H_2NOR^1 \cdot HCl$ in a suitable reaction inert solvent and in the presence of a base. Suitable solvents include water/lower alcohols, methylene chloride and chloroform, with ethanol/water being preferred. Suitable bases include sodium acetate, pyridine or triethylamine. The reaction may be conducted at a temperature from about 0° to about 150° C. From about 30° to about 70° C. is preferred.

Scheme 6 illustrates a method of synthesizing compounds having the formulae I-O, I-P and I-Q from the corresponding compounds of the formula I-B. Compounds of the formula I-O may be prepared by reacting the corresponding compounds of the formula I-B with a reducing agent. Suitable reducing agents include sodium borohydride and lithium aluminum hydride. Solvents appropriate for use with sodium borohydride include lower alcohols, with methanol or ethanol being preferred. Solvents appropriate for use with lithium aluminum hydride include THF, ether and dioxane, with THF being preferred. Generally, this reaction is conducted at temperatures from about room temperature to 100° C. The preferred temperature is 30° C.

The compounds of the formula I-O prepared by the foregoing procedure may be converted to the corresponding compounds of the formula I-P, wherein ring D contains a double bond between the carbons at positions "1" and "2" or between the carbons at positions "2" and "3" by first converting them to the corresponding acetate, mesylate or tosylate derivatives wherein the acetate, mesylate or tosylate group replaces the hydroxy group, according to the procedures described above for converting compounds of the formula I-M to, respectively, the acetate, mesylate or tosylate derivatives thereof, and then subjecting the derivatives formed thereby to an elimination reaction. The elimination reaction is typically carried out using a base such as diazabicycloundecane or diazabicyclononane in a suitable reaction inert solvent, at a temperature from about 0° to about 100° C., preferably from about 0° to about 100° C. Suitable solvents include methylene chloride, chloroform and THF. Methylene chloride is preferred.

Compounds of the formula I-Q, wherein ring D contains a double bond between the carbons at positions "1" and "2" or between the carbons at positions "2" and "3" and wherein $R^{11}$ and the hydrocarbon chain containing P are attached to adjacent carbons of ring D connected by a double bond, may be prepared from the corresponding compounds of the formula I-B. This is accomplished by reacting the appropriate compound of the formula I-B with a compound of the formula $R^{11}MgX$, wherein X is chloro, bromo, or iodo, in a suitable reaction inert solvent, and then adding, successively, a dilute acid such as dilute hydrochloric acid, dilute sulfuric acid or dilute phosphoric acid, and a base such as a saturated solution of sodium bicarbonate or sodium hydroxide. Generally, this reaction is conducted at temperatures from about −78° to about 100° C., preferably from about 0° C. to about room temperature for the addition of $R^{11}MgX$, and at about room temperature for the addition of the acid. Examples of suitable solvents for the reaction with $R^{11}MgX$ are THF, ether and toluene.

Scheme 9 illustrates the preparation of compounds having the formula I-R. These are compounds of the formula I wherein the carbon at position 2 of ring D is replaced nitrogen, an oxo group (=O) is attached to the carbon at position 1 of the same ring, q is 2 and M is carbon.

Compounds of the formula I-R may be prepared by first subjecting the appropriate compound of the formula VII to reductive amination using a compound of the formula

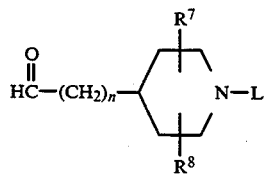

and a reducing agent such as sodium cyanoborohydride, sodium triacetoxyborohydride or sodium borohydride. The reductive amination is carried out in a suitable reaction inert solvent such as acetic acid, a lower alcohol, THF or mixtures containing a lower alcohol and THF, at a temperature from about 0° C. to about 60° C. Preferably, it is carried out at about room temperature in acetic acid or a THF/lower alcohol mixture.

The foregoing reaction yields a compounds of the formula VIII. Acid or base hydrolysis of this compound followed by amide formation yields the corresponding compound of formula I-R. When R is ($C_1$–$C_8$) alkyl, compound of the formula VIII are hydrolyzed by base hydrolysis. Examples of bases that may be used include lithium and sodium hydroxide (lithium hydroxide is preferred). Suitable solvents include dioxane/water, ether/water, THF/water, and ($C_1$–$C_5$) alkanol/water. Dioxane/water is preferred. When R is benzyl, compounds of the formula VIII are hydrolyzed under acidic conditions using, for example, aqueous hydrogen bromide in acetic acid. Alternatively, such compounds (e.g., wherein R is benzyl) may be hydrogenated using palladium on carbon in a ($C_1$–$C_4$) alkanol to yield the corresponding compounds of formula IX. The hydrolysis reaction is generally run at a temperature from about 20° C. to about 120° C., preferably at about 25° C.

Compounds of the formula IR may be prepared by subjecting the corresponding compounds of formula IX to lactam formation conditions. The reagent typically used for the lactam formation is a dialkylcarbodiimide such as N-ethyl-N'-[2-(dimethylamino)ethyl]carbodiimide (EDEC), N-ethyl-N'-[2-(dimethylamino)propyl]-carbodiimide (EDPC), 1-cyclohexyl-3-(2-morpholinoethyl)carbodiimide metho-p-toluenesulfonate (CMCMT) or dicyclohexylcarbodiimide. EDEC or CMCMT is preferred. This reaction is usually carried out in an aprotic solvent such as DMF or pyridine in the presence of a base at a temperature from about 10° C. to about 60° C., preferably at about room temperature.

Alternatively, the lactam formation step may be carried out using titanium IV isoproxide in dichloroethane at a temperature from about 20° C. to about 100° C., preferably from about 60° C. to about 85° C.

It is preferable to prepare certain of the compounds of the formula I by "the following methods rather than those described above due to the nature of the $R^3$ to $R^6$ substituents.

When one of the $R^3$ to $R^6$ substituents is $CONHR^9$, the final product of formula I may be prepared from the corresponding compound of the formula I wherein such substituent is $COOR^9$ by acid or base hydrolysis, followed by reaction with thionyl chloride and a compound of the formula $R^9NH_2$. The acid hydrolysis is generally carried out using 2N-6N hydrochloric acid and the base hydrolysis is generally carried out using lithium, potassium or sodium hydroxide in water or a lower alcohol/water solvent. Temperatures for both the acid and base hydrolysis generally range from about room temperature to about 100° C. About 100° C. is preferred. The reaction with thionyl chloride, which yields the corresponding acyl chloride, is typically carried out in a reaction inert solvent such as methylene chloride, THF or chloroform, at a temperature from about 80° to about 120° C., preferably at about 100° C. The reaction of the acyl chloride with RgNH is typically carried out in a reaction inert solvent such as methylene chloride, THF or chloroform, preferably methylene chloride, at a temperature from about room temperature to about 150° C. preferably from about 30° to about 80° C.

When one of the $R^3$ to $R^6$ substituents is $NR^9R^{10}$, the final product of formula I may be prepared by reduction of the corresponding compound of the formula I wherein such substituent is nitro, to first produce the corresponding compound wherein such substituent is $R^9NH$, followed by reductive amination. This process may be carried out as follows. First, the nitro compound is hydrogenated or reacted with a metal and an acid to yield the corresponding amine. The hydrogenation is typically carried out using hydrogen and a catalyst such as palladium on charcoal, at a temperature from about 0 to about 100° C., preferably at about room temperature, and at a pressure from about 1 to about 6 atm, preferably about 3 atm. The reduction using a metal and an acid is generally carried out using a metal such as iron or zinc, and an acid such as concentrated hydrochloric acid. Suitable temperatures for this reaction range from about 0° to about 150° C. Temperatures from about 80° to about 120° C. are preferred.

After the reduction via hydrogenation or reaction with a metal and an acid, a compound of the formula

is added to the resulting amine, followed by either lithium aluminum hydride, diborane dimethyl- sulfide or diborane. Examples of suitable solvents for the addition of lithium aluminum hydride are THF, ether, and dioxane. THF is preferred. Suitable solvents for the addition of diborane dimethylsulfide or diborane include THF and ether. THF is preferred. The reaction with lithium aluminum hydride, diborane dimethylfulfide, or diborane is typically carried out at temperatures from about room temperature to about 100° C., preferably from about 60° to about 80° C.

Alternatively, compound of the formula

may be added to the resulting amine in an appropriate solvent and in the presence of a base, at a temperature from about 0°to about 100° C., preferably from about 10° to about 40° C. This reaction is followed by reduction with sodium cyanoborohydride or sodium borohydride to give the corresponding compound of the formula $CONHR^9$. Sodium cyanoborohydride is preferred. Lower alcohols and acetic acid are examples of suitable solvents.

The reactions with

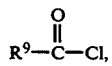

lithium aluminum hydride (or diborane dimethylsulfide or diborane) or

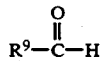

are the repeated in the manner described above, but replacing

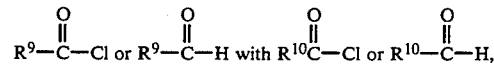

to give the final product of formula I, wherein one of $R^3$ to $R^6$ is $CONR^9R^{10}$.

When one of $R^3$ to $R^6$ is a hydroxy group, the final product having formula I may be prepared via base hydroysis of the corresponding compound of formula I wherein such substituent is rosylate. The base hydrolysis is typically performed using a base such as sodium or potassium hydroxide or a sodium alkoxide, in a suitable reaction inert solvent such as a mixture of a lower alcohol and water or a lower alcohol alone, at a temperature from about room temperature to about 120° C., preferably about 80°to about 100° C. The reaction mixture is then neutralized using a dilute acid such as hydrochloric acid or phosphoric acid.

In each of the above reactions, pressure is not critical. Pressures in the range of about 0.5 atm to 3 atm are suitable, and ambient pressure (generally, about one atmosphere) is preferred as a matter of convenience. Also, for those reactions where the preferred temperature varies with the particular compounds reacted, no preferred temperature is stated. For such reactions, preferred temperatures for particular reactants may be determined by monitoring the reaction using thin layer chromatography.

The compounds of the invention may be administered to a patient by various methods, for example, orally as capsules or tablets, parentally as a sterile solution or suspension, and in some cases, intravenously in the form of a solution. The free base compounds of the invention may be formulated and administered in the form of their pharmaceutically acceptable acid addition salts.

The daily dose of the compounds of the invention is generally in the range of from about 1 to 300 mg/day for the average adult human, and may be administered in single or divided doses.

When incorporated for parenteral administration into a solution or suspension, the compounds of the invention are present in a concentration of at least 1 weight percent, and preferably between about 4–70 weight percent (based on the total weight of the unit). The parenteral dosage unit typically contains between about 5 to 100 mg of active compound(s).

Compounds of the present invention may be administered orally with an inert diluent or an edible carrier, or they may be enclosed in gelatin capsules or compressed into tablets. Such preparations should contain at least 0.5% of active compound(s), but the concentration may vary depending upon the particular form and may be from 4 to 70 weight percent (based on the total weight of the unit). The oral dosage unit typically contains between 1.0 mg to 300 mg of active compound.

The activity of the compounds of the present invention as cholinesterase inhibitors may be determined by a number of standard biological or pharmacological tests. One such procedure for determining cholinesterase inhibition is described by Ellman et al. in "A New and Rapid Colorimetric Determination of Acetylcholinesterase Activity", Biochem. Pharm. 1, 88, (1961).

The present invention is illustrated by the following examples. It will be understood, however, that the invention is not limited to the specific details of these examples. Melting points are uncorrected. Proton nuclear magnetic resonance spectra ($^1H$ NMR) and $C^{13}$ nuclear magnetic resonance spectra ($C^{13}$ NMR) were measured for solutions in deuterochloroform ($CDCl_3$) and peak positions are expressed in parts per million (ppm) downfield from tetramethylsilane (TMS). The peak shapes are denoted as follows: s, singlet; d, doublet; t, triplet; q, quartet; m, multiplet; b, broad.

EXAMPLE 1

Ethyl-1-benzyleridine-4-carboxylate

A mixture of ethyl isonipecotate (69.25 g, 0.441 mol). -bromotoluene (75.44 g, 52.4 ml, 0.441 mol) and triethylamine (44.74 g, 61.5 ml, 0.441 mol) in 1000 ml methylene chloride was stirred at r.t. for 20 hr. The mixture was washed with brine and the organic layer was separated, dried and concentrated to give 97.016 g of ethyl 1-benzylpiperidine-4-carboxylate as a yellow oil. HNMR ($CDCl)\delta$ 1.2(t, 3H), 1.6–1.9 (m, 4H), 2.0 (dt, 2H), 2.2–2.3 (m, 1H), 2.85 (m, 2H), 3.5 (s, 2H), 4.1 (q, 2H), 7.2–7.36 (m, 5H) ppm.

EXAMPLE 2

1-benzypiperidine-4-carboxaldehyde

To a solution of ethyl 1-benzylpiperidine-4-carboxylate (9.2 g, 0.037 mol) in 400 ml of toluene was added 1.5M diisobutylaluminum hydride in toluene (28 ml, 0.042 mol) at $-78°$ C. The mixture was stirred at $-78°$ C. for 1 hr and quenched with 150 ml of MeOH and the dry ice bath was removed. After stirring for 2 hr at r.t., the mixture was filtered through diatomaceous earth (Celite (trademark)) and washed with methanol. The filtrate was concentrated to dryness to give 6.91 g (92%) of 1-benzylpiperidine-4-carboxaldehyde which can be used directly or purified by vacuum distillation, bp 93°–97° C./1 mmHg. HNMR ($CDCl_3)\delta$ 1.6–1.8 (m, 2H), 1.8–1.9 (m, 2H), 2.05–2.17 (m, 2H), 2.17–2.3 (m, 1H), 2.75–2.9 (m, 2H), 3.5 (s, 2H), 7.2–7.4 (m, 5H), 9.6 (s, 1H) ppm.

EXAMPLE 3

2,3-dihydro-1-oxo-1H-pyrrolo[1.2-a]indole

A stirred solution of ethyl indole-2-carboxylate (5.67 g, 30 mmol) in 400 ml of toluene under N was treated with sodium hydride (1.44 g, 36 mmol). Ethyl acrylate (3.6 ml, 33 mol) was added and the mixture was heated at reflux. Additional portions of ethyl acrylate (6 mmol) and sodium hydride (16 mmol) were added after 3 hr. After a total time of 6 hr, t.l.c. indicated that all starting material are consumed. The mixture was quenched with ethanol and treated with water, dilute HCl, and methylene chloride. The organic phase was washed with brine, dried over sodium sulfate, filtered, and concentrated to give 2,3-dihydro-1-oxo-2-ethoxycarbonyl-1H-pyrrolo[1,2-a]indole, which was used directly in the next step.

A solution of 2,3-dihydro-1-oxo-2-ethoxycarbonyl-1H-pyrrolo[1,2-a]indole in 400 mL of acetic acid and 25 mL of water was heated at reflux under $N_2$ for 16 hr. The resulting solution was cooled and concentrated to dryness. The residue was treated with water and methylene chloride. The organic layer was washed with $NaHCO_3$, brine, dried and concentrated to give solid which was purified by column chromatography to give the title compound. HNMR ($CDCl_3)\delta$ 2.17 (t, 2H), 4.38 (t, 2H), 6.95 (s, 1H), 7.06–7.2 (m, 1H), 7.2–7.4 (m, 1H), 7.7 (d, 1H) ppm.

EXAMPLE 4

2,3-dihydro-1-oxo-7-methoxy-1H-pyrrolo[1,2-a]indole

A stirred solution of ethyl 5-methoxy-indole-2-carboxylate (30 g, 137 mmol) in 1.5 L of toluene under $N_2$ was treated with sodium hydride (6.7 g of 60% in oil, 167 mmol) and ethylacrylate (16.3 ml, 150 mmol). The mixture was heated to reflux. After 3 hours (hr), additional ethyl acrylate (3 ml) and sodium hydride (3.3 g) were added. After a total of 8 hr, the starting material was consumed completely and the mixture was quenched with ethanol and treated with water and dilute HCl and methylene chloride. The organic layer was washed with brine, dried and concentrated to give 2,3-dihydro-1-oxo-7-methoxy-2-ethoxycarbonyl-1H-pyrrolo[1,2-a]indole, which was used directly in the next step.

A solution of the compound produced in the previous step in 2.0 L of acetic acid and 100 ml of water was heated at reflux under $N_2$ for 20 hr. The reaction mixture was cooled to r.t. and concentrated. The residue was treated with water and extracted with methylene chloride. The organic layer was washed with saturated sodium bicarbonate, brine, dried and concentrated to give brown solid. The brown solid was purified through silica gel to give the title compound. 1HNMR ($CDCl_3)\delta$ 3.15 (t, 2H), 3.8 (s, 3H), 4.4 (t, 2H), 6.9 (s, 1H), 6.96–7.1 (m, 2H), 7.2–7.3 (m, 1H) ppm.

The title compounds of Examples 5–14 were prepared using a method analogous to that described in Examples 3 and 4, starting from the corresponding substituted ethyl indole-2-carboxylate:

EXAMPLE 5

2,3-dihydro-1-oxo-6,7-dimethoxy-1H-pyrrolo[1-,2a]indole was prepared starting from ethyl 5,6-dimethoxy-indole-2 -carboxylate. HNMR ($CDCl_3)\delta$ 3.2 (t, 2H), 3.9 (s, 3H), 4.0 (s, 3H), 4.4 (t, 2H), 6.75 (s, 1H), 6.9 (s, 1H), 7.1 (s, 1H) ppm.

EXAMPLE 6

2,3-dihydro-1-oxo-7-fluoro-1H-pyrrolo[2a]indole was prepared starting from ethyl 5-fluoro-indole-2-carboxylate. 1HNMR ($CDCl_3)\delta$ 3.25 (t, 2H), 4.4 (t, 2H), 6.9 (s, 1H), 7.1–7.2 (m, 1H), 7.2–7.5 (m, 2H) ppm.

EXAMPLE 6

2,3-dihydro-1-oxo-7-methyl-1H-pyrrolo[1,2-a]indole was prepared starting from ethyl 5-methyl-indole-2-carboxyate. HNMR ($CDCl_3)\delta$ 2.46 (s, 3H), 3.2 (t, 2H), 4.4 (t, 2H), 6.9 (s, 1H), 7.1–7.4 (m, 2H), 7.5 (s, 1H) ppm.

EXAMPLE 8

L-dihydro-1-oxo-6-methyl-1H-pyrrolo[a]indole was prepared starting from ethyl 6-methyl-indole-2-carboxylate. 1HNMR ($CDCl_3)\delta$ 2.48 (s, 3H), 3.2 (t, 2H), 4.4 (t, 2H), 6.96 (s, 1H), 7.0 (d, 1H), 7.2 (s, 1H), 7.65 (d, 1H) ppm.

EXAMPLE 9

2,3-dihydro-1-oxo-6-methoxy-1H-pyrrolo[1,2-a]indole was prepared starting from ethyl 6-methoxy-indole-2-carboxylate. HNMR ($CDCl)\delta$ 3.2 (t, 2H), 3.9 (s, 3H), 4.4 (t, 2H), 6.75 (d, 1H), 6.85 (dd, 1H), 6.5 (s, 1H), 7.6 (d, 2H) ppm.

EXAMPLE 10

23-dihydro-1-oxo-7-ethoxy-1H-pyrrolo[2-a]indole was prepared starting from ethyl 5-ethoxy-indole-2-carboxylate. HNMR (CDCl$_3$)δ 1.4 (t, 3H), 3.17 (t, 2H), 4.0 (q, 2H), 4.4 (t, 2H), 6.85 (s, 1H), 6.9–7.1 (m, 2H), 7.28 (d, 1H) ppm.

EXAMPLE 11

2,3-dihydro-1-oxo-7-benzyloxy-1H-pyrrolo[1,2a]indole was prepared starting from ethyl 5-benzyloxy-indole-2-carboxylate. $^1$HNMR (CDCl$_3$)δ 3.2 (t, 2H), 4.4 (t, 2H), 5.1 (s, 2H), 6.9 (s, 1H), 7.1–7.6 (m, 8H) ppm.

EXAMPLE 12

2,3-dihydro-1-oxo-8-methyl-1H-pyrrolol[1,2-a]indole was prepared starting from ethyl 4-methyl-indole-2-carboxylate. $^1$HNMR (CDCl$_3$)δ 2.54 (s, 3H). 3.16 (t, 2H), 4.18 (t, 2H), 6.9 (t, 1H), 6.98 (s, 1H), 7.2 (m, 1H) ppm.

EXAMPLE 13

2,3-dihydro-1-oxo-8-methoxy-1H-pyrrolo[1,2-a]indole was prepared starting from ethyl 4-methoxy-indole-2-carboxylate. $^1$HNMR (CDCl$_3$)δ 3.2 (t 2H), 3.95 (s, 1H), 4.4 (t, 2H), 6.5 (d, 1H), 7.0 (d, 1H), 7.3 (m, 2H) ppm.

EXAMPLE 14

2,3-dihydro-1-oxo-7-p-tosyloxy-1H-pyrrolo[1,2-a]indole was prepared starting from ethyl 5-p-tosyloxy-indole-2-carboxylate. $^1$HNMR (CDCl$_3$)δ 2.4 (s, 3H), 3.2 (t, 2H), 4.4 (t, 2H), 6.9 (s, 1H), 7.0 (dd, 1H), 7.2–8.4 (m, 4H), 7.67 (d, 2H) ppm.

EXAMPLE 15

1-benzyl-4-[2,3-dihydro-1-oxo-1H-pyrrolo[1,2a]indolo)-2ylidenyl]methylpiperidine:

To a solution of the title compound of Example 3 (1.71 g, 10 mmol) in 50 ml of anhydrous THF, was added sodium hydride (60% in mineral oil, 0.42 g, 10.5 mmol) at 0° C. After 5 min. a solution of 1-benzylpiperidine-4-carboaldehyde (2.03 g, 10 mmol) in anhydrous THF was added at 0C. After 5 min. the mixture was stirred at room temperature (r.t.) for an additional 30 min and thin layer chromatography (t.l.c.) showed the starting material had disappeared completely. The mixture was quenched with brine and extracted with ethyl acetate. The organic layer was washed with water, dried and concentrated to give the crude product which was purified through silica gel column chromatogrpahy to give the title compound as pale-white solid. $^1$HMR (CDCl$_3$)δ 1.5–1.7 (m, 4H), 1.9–2.1 (m, 2H), 2.1–2.4 (m, 1H), 2.8–3.0 (m, 2H), 3.5 (s, 2H), 4.9 (ABq, 2H), 6.7 (dd, 1H), 7.9 (s, 1H), 7.1–7.4 (m, ell), 7.7 (d, 1H) ppm.

EXAMPLE 16

2,3-dihydro-7-methoxy2-[[(phenylmethyl)-4-piperidinyl]methylene]-1H-pyrrolo[1,2-a]indol-1-one To a solution of the title compound of Example 4 (5,739 g, 28.5 mmol) in 400 ml dry THF was added sodium hydride (60% in mineral oil, 1.282 g, 32.1 mmol), then 1-benzylpiperidine-4-carboxaldehyde (6.14 g, 30.2 mmol) at 0° C. The ice-bath was removed and the mixture was stirred at r.t. for 30 min (t.l.c. showed no starting material left). The mixture was quenched with 100 ml of saturated ammonium chloride and 300 ml of ethyl acetate. The organic layer was washed with brine, dried and concentrated to give 10.268 g of yellow-brown solid which was purified through silica gel to give 8.790 g (80% yield) of the title compound as a pale-white solid. HNMR (CDCl$_3$)δ 1.5–1.75 (m, 4H), 1.9–2.15 (m, 2H), 2.15–2.4 (m, 1H), 3.5 (s, 2H), 3.85 (s, 3H), 4.9 (ABq, 2H), 6.7 (dd, 1H), 6.95 (s, 1H), 7.0–7.15 (m, 2H), 7.2–7.4 (m, 6H) ppm.

The title compounds of Examples 17–27 were prepared using a method similar to that described in Examples 15 and 16, starting from the corresponding substituted 2,3-dihydro-1-oxo-1H-pyrrolo[1,2-a]indole.

EXAMPLE 17

2,3-dihydro-6,7-dimethoxy-2-[[1-(phenylmethyl)-4-piperidinyl]methylene]1H-pyrrolo[1,2-a]indol-1-one was prepared starting from the title compound of Example 5. $^1$HNMR (CDCl$_3$)δ 1.5–1.7 (m, 4H), 1.9–2.1 (m, 2H), 2.1–2.3 (m, 1H), 3.5 (s, 2H), 3.9 (s, 3H), 3.94 (s, 3H), 4.9 (ABq, 2H), 6.64 (dd, 1H), 6.72 (s, 1H), 6.96 (s, 1H), 7.04 (s, 1H), 7.2–7.3 (m, 5H) ppm.

EXAMPLE 18

2,3-dihydro-7-fluoro-2-[[1-(phenylmethyl)-4-piperidinyl]-methylene]-1H-pyrrolo[1,2-a]indol-1-one was prepared starting from the title compound of Example 6. $^1$HNMR (CDCl$_3$) δ 1.5–1.7 (m, 4H), 2.0–2.15 (m, 2H), 2.15–2.4 (m, 1H), 2.8–3.0 (m, 2H), 3.55 (s, 2H), 4.95 (ABq, 2H), 6.75 (dd, H), 7.0 (s, 1H), 7.1–7.2 (m, 1H), 7.2–7.4 (m, 7H) ppm.

EXAMPLE 19

2,3-dihydro-7-methyl-2-[[1-(phenylmethyl)-4-piperidinyl]methylene-1H-pyrrolo]1,2-a]indol-1-one was prepared starting from the title compound of Example 7. $^1$HNMR (CDCl$_3$)δ 1.5–1.8 (m, 4H), 1.9–2.15 (m, 2H), 2.15–2.35 (m, 1H), 2.42 (s, 3H), 2.8–3.0 (m, 2H), 3.52 (s, 2H), 4.88 (ABq, 2H), 6.7 (dd, 1H), 6.96 (s, 1H), 7.1–7.4 (m, 7H), 7.5 (s, 1H) ppm.

EXAMPLE 20

2,3-dihydro-6-methyl-2-[[1-(phenylmethyl)-4-piperidinyl]methylene-1H-pyrrolo]1,2-a]indol-1-one was prepared starting from the title compound of Example 8. $^1$HNMR (CDCl$_3$)δ 1.5–1.8 (m, 4H), 2.0–2.15 (m, 2H), 2.15–2.35 (m, 1H), 2.5 (s, 3H), 2.95 (m, 2H), 3.55 (s, 2H), 4.95 (ABq, 2H), 6.75 (m, 1H), 7.0 (d, 1H), 7.05 (s, 1H), 7.15–7.4 (m, 6H), 7.65 (d, 1H) ppm.

EXAMPLE 21

2,3-dihydro-6-methyl-2-[[1-(phenylmethyl)-4-piperidinyl]methylene-1H-pyrrolo]1,2-a]indol-1-one was prepared starting from the title compound of Example 9. $^1$HNMR (CDCl$_3$)δ 1.55–1.8 (m, 4H), 2.0–2.15 (m, 2H), 2.15–2.4 (m, 1H), 2.95 (m, 2H), 3.5 (s, 2H), 3.9 (s, 3H), 4.9 (ABq, 2H), 6.7 (m, 2H), 6.85 (dd, 1H), 7.05 (s, 1H), 7.2–7.4 (m, 5H), 7.6 (d, 1H) ppm.

EXAMPLE 22

2,3-dihydro-7-methyl-2-[[1-(phenylmethyl)-4-piperidinyl]methylene-1H-pyrrolo]1,2-a]indol-1-one was prepared starting from the title compound of Example 10. $^1$HNMR (CDCl$_3$)δ 1.4 (t, 3H), 1.5–1.8 (m, 4H), 2.0–2.15 (m, 2H), 2.2–2.4 (m, 1H), 2.85–3.0 (m, 2H), 3.5 (s, 2H), 4.05 (g, 2H), 4.95 (ABg, 2H), 6.7 (m, 1H), 6.98 (s, 1H), 7.0–7.1 (m, 2H), 7.2–7.4 (m, 6H) ppm.

EXAMPLE 23

2,3-dihydro-7-methyl-2-[[1-(phenylmethyl)-4-piperidinyl]methylene-1H-pyrrolo]1,2-a]indol-1-one was prepared starting from the title compound of Example 11. $^1$HNMR (CDCl$_3$)δ 1.5–1.8 (m, 4H), 2.0–2.15 (m, 2H), 2.15–2.4 (m, 1H), 2.9–3.0 (m, 2H), 3.55 (s, 2H), 4.9 (d, 2H), 5.1 (s, 2H), 6.7 (m, 1H), 7.0 (s, 1H), 7.1–7.2 (m, 2H), 7.2–7.5 (m, 11H) ppm.

EXAMPLE 24

2,3-dihydro-8-methyl-2-[[1-(phenylmethyl)-4-piperidinyl]methylene-1H-pyrrolo]1,2-a]indol-1-one was prepared starting from the title compound of Example 12. $^1$HNMR (CDCl$_3$)δ 1.5–1.8 (m, 4H), 1.9–2.1 (m, 2H), 2.1–2.3 (m, 1H), 2.5 (s, 3H), 2.9 (m, 2H), 3.5 (s, 2H), 4.9 (ABq, 2H), 6.7 (m, 1H), 6.9 (d, 1H), 7.05 (s, 1H)$_{7.1-7.3}$ (m, 7H) ppm.

EXAMPLE 25

2,3-dihydro-8-methyl-2-[[1-(phenylmethyl)-4-piperidinyl]methylene-1H-pyrrolo]1,2-a]indol-1-one was prepared starting from the title compound of Example 13. $^1$HNMR (CDCl$_3$)δ 1.55–2.1 (m, 6H), 2.15–2.35 (m, 1H), 2.95 (m, 2H), 3.55 (s, 2H), 3.95 (s, 3H), 4.95 (ABq, 2H), 6.5 (d, 1H), 6.7 (m, 1H), 7.0 (d, 1H), 7.2–7.4 (m, 7H) ppm.

EXAMPLE 26

2,3-dihydro-7(p-tosyloxy)-2-[[1-(phenylmethyl)-4-piperidinyl]methylene-1H-pyrrolo]1,2-a]indol-1-one was prepared starting from the title compound of Example 14. $^1$HNMR (CDCl$_3$)δ (1.4–1.7 (m, 4H), 1.95–2.1 (m, 2H), 2.1–2.3 (m, 1H), 2.4 (m, 3H), 2.9 (m, 2H), 3.5 (s, 2H), 4.9 (ABq, 2H), 6.7 (m, 1H), 6.94 (s, 1H), 7.0 (dd, 1H), 7.15–7.35 (m, 9H), 7.65 (d, 2h) ppm.

EXAMPLE 27

2,3-dihydro-9-methyl-2-[[1-(phenylmethyl)-4-piperidinyl]methylene-1H-pyrrolo]1,2-a]indol-1-one was prepared starting from 2,3-dihydro-1-oxo-9-methyl-1-pyrrolo[1,2-a]indole $^1$HNMR (CDCl)δ 1.5–1.8 (m, 4H), 1.95–2.1 (m, 2H), 2.1–2.3 (m, 1H), 2.6 (s, 3H), 2.9 (m, 2H), 3.52 (s, 2H), 4.88 (ABq, 2H), 6.66 (dd, 1H), 7.1–7.4 (m, H), 7.68 (d, 1H) ppm.

EXAMPLE 28

2,3-dihydro-2-[[1-phenylmethyl)-4-piperidinyl]methyl]-1H-pyrrolo]1,2-a]indol-1-one The title compound of Example 15 (650 mg, 1.83 ol) was dissolved in a mixture of solvents of EtOAc (40 mL), THF (70 ml) and methanol (50 mL) and treated with PtO$_2$ (70 mg) and hydrogenated at 45 psi and at room temperature for 1 hour (t.l.c. indicated no starting material left). The mixture was filtered through diatomaceous earth (Celite (trademark)). The filtrate was concentrated to dryness to give the title compound as a pale-white solid. $^1$HNMR (CDCl$_3$) δ 1.2–1.8 (m, 6H), 1.8–2.1 (m, 3H), 2.8–3.0 (m, 2H), 3.15–3.3 (m, 1H), 3.45 (s, 2H), 3.95 (dd, 1H), 4.55 (dd, 1H), 6.93 (s, 1H), 7.0–7.4 (m, 8H), 7.65 (d, 1H) ppm.

EXAMPLE 29

2,3-dihydro-7-methyl-2-[[1-(phenylmethyl)-4-piperidinyl]methylene-1H-pyrrolo]1,2-a]indol-1-one The title compound of Example 16 (4.702 g, 12.2 ol) was dissolved in a mixture of solvents of ethyl acetate (500 ml) and ethanol (500 ml) and treated with PtO (511 mg) and hydrogenated at 30 psi at r.t. for 1.25 hr. The mixture was filtered through diatomaceous earth (Celite (trademark)) and the filtrate was concentrated to give 4,730 g (99.8%) of the title compound as a beige solid which was recrystallized from ethyl acetate to give white crystals. H (CDCl$_3$)δ 1.2–1.8 (m, 6H), 1.82–2.1 (m, 3H), 2.77–2.99 (m, 2H), 3.08–3.24 (m, 1H), 3.44 (s, 2H), 3.8 (s, 3H), 3.9 (dd, 1H), 4.48 (d, 1H), 6.9 (s, 1H), 6.9–7.1 (2H), 7.1–7.3 (m, 6H) ppm. The title compound was resolved with (S)-mandelic acid and (R)-mandelic acid to give the corresponding (−) and (+) enantiomers, respectively, having $[\alpha]_D^{25}$ values of −6.3° and +3°, respectively.

The title compounds of Examples 30–40 were prepared by a method analogous to that described in examples 28 and 29, starting from the corresponding title compounds of Examples 7–27.

EXAMPLE 30

2,3-dihydro-6,7-methyl-2-[[1-(phenylmethyl)-4-piperidinyl]methylene-1H-pyrrolo]1,2-a]indol-1-one was prepared starting from the title compound of Example 17. $^1$HNMR (CDCl$_3$)δ 1.2–1.8 (m, 6H), 1.8–2.2 (m, 3H), 2.8–2.95 (m, 2H), 3.15–3.3 (m, 1H), 3.5 (s, 2H), 3.9 (s, 3H), 3.95 (s, 3H), 4.0 (dd, 1H), 4.55 (dd, 1H), 6.75 (s, 1H), 6.9 (s, 1H), 7.06 (s, 1H), 7.25–7.4 (m, 5H) ppm.

EXAMPLE 31

2,3-dihydro-7-fluoro-2]]1-phenylmethyl)-4-piperidinyl]methylene-1H-pyrrolo]1,2-a]indol-1-one was prepared starting from the title compound of Example 18. $^1$HNMR (CDCl$_3$)δ 1.2–1.8 (m, 6H), 1.8–2.2 (m, 3H), 2.8–3.0 (m, 2H), 3.15–3.3 (m, 1H), 3.5 (s, 2H), 4.0 (dd, 1H), 4.6 (dd, 1H), 4.6 (dd, 1H), 6.9 (s, 1H), 7.1–7.2 (m, 1H), 7.2–7.4 (m, 7H) ppm.

EXAMPLE 32

2,3-dihydro-7-methyl-2-[[1-(phenylmethy)-4-piperidinyl]methyl]-1H-pyrrolo[1,2-a]indol-1-one was prepared from the title compound of Example 19. $^1$HNMR (CDCl)δ 1.2–1.8 (m, 6H), 1.8–2.1 (m, 3H), 2.45 (s, 3H), 2.85–3.05 (m, 2H), 3.1–3.3 (m, 1H), 3.5 (s, 2H), 3.95 (dd, 1H), 4.5 (dd, 1H), 6.85 (s, 1H), 7.1–7.4 (m, 7H), 7.5 (s, 1H) ppm.

EXAMPLE 33

2,3-dihydro-6-methyl-2O[[1-(phenylmethyl)-4-piperidinyl]methyl]-1H-pryrrolo[1,2-a]indol-1-one was prepared starting from the title compound of Example 20. $^1$HNMR (CDCl)δ 1.4–1.7 (m, 4H), 1.7–1.85 (m, 2H), 2.0. –2.2 (m, 3H), 2.5 (s, 3H), 3.0 (m, 2H), 3.15–3.3 (m, 1H), 3.6 (s, 2H), 4.0 (dd, 1H), 4.55 (dd, 1H), 6.95 (s, 1H), 7.0 (d, 1H), 7.2 (s, 1H), 7.2–7.4 (m, 5H), 7.6 (d, 1H) ppm.

EXAMPLE 34

2,3-dihydro-6-methoxy-2-[[1-(phenylmethyl)-4-piperidinyl]methyl]-1H-pyrrolo]1,2-a]indol-1-one was prepared starting from the title compound of Example 21. $^1$HNMR (CDCl$_3$)δ 1.3–1.8 (m, 6H), 1.9–2.2 (m, 3H), 2.8–3.0 (m, 2H), 3.15–3.3 (m, 1H), 3.5 (s, 2H), 3.85 (s, 3H), 3.95 (dd, 1H), 4.55 (dd, 1H), 6.7 (s, 1H), 6.85 (dd, 1H), 6.9 (s, 1H), 7.2–7.4 (m, 5H), 7.6 (d, 1H) ppm.

EXAMPLE 35

3-dihydro-7-ethoxy-2-[[1-(phenylmethyl)-4-piperidinyl]methyl]-1H-pyrrolo[1,2-a]indol-1-one was prepared starting from the title compound of Example 22. $^1$HNMR (CDCl$_3$)δ 1.4–1.6 (m, 7H), 1.6–1.8 (m, 2H), 1.9–2.1 (m, 3H), 2.9 (m, 2H), 3.25 (m, 1H), 3.5 (s, 2H), 3.95 (dd, 1H), 4.05 (q, 2H), 4.55 (dd, 1H), 6.9 (s, 1H), 7.0–7.1 (m, 2H), 7.1–7.4 (m, 6H) ppm.

EXAMPLE 36

2,3-dihydro-7-benzyloxy-2-[[1-(phenylmethyl)-4-piperidinyl]methyl]-1H-pyrrolo[1,2-a]indol-1-one was prepared starting from the title compound of Example 23. $^1$HNMR (CDCl$_3$)δ 1.2–1.8 (m, 6H), 1.9–2.1 (m, 3H), 2.9 (m, 2H), 3.25 (m, 1H), 3.55 (s, 2H), 4.0 (dd, 1H), 4.6 (dd, 1H), 5.1 (s, 2H), 6.9 (s, 1H), 7.05–7.2 (m, 2H), 7.2–7.5 (m, 11H) ppm.

EXAMPLE 37

2,3-dihydro-8-methyl-2-[[1-(phenylmethyl)-4-piperidinyl]methyl]-1H-pyrrolo[1,2-a]indol-1-one was prepared starting from the title compound of Example 24. $^1$HNMR (CDCl$_3$) δ 1.3–1.8 (m, 6H), 1.9–2.2 (m, 3H), 2.55 (s, 3H), 2.9 (m, 2H), 3.2–3.35 (m, 1H), 3.5 (s, 2H), 4.0 (dd, 1H), 4.6 (dd, 1H), 6.95 (d,1H), 7.0 (s, 1H), 7.2–7.4 (m, 7H) ppm.

EXAMPLE 38

2,3-dihydro-8-methoxy-2-[[-(phenylmethyl)-4-piperidinyl]methyl]-1H-pyrrolo[1,2-a]indol-1-one was prepared starting from the title compound of Example 25. $^1$HNMR (CDCl) δ 1.3–1.8 (m, 6H), 1.9–2.1 (m, 3H), 2.9 (m, 2H), 3.15–3.35 (m, 1H), 3.5 (s, 2H), 3.95 (s, 3H), 4.0 (dd, 1H), 4.6 (dd, 1H), 6.5 (d, 1H), 6.95 (d, 1H), 7.1 (s, 1H), 7.2–7.4 (m, 6H) ppm.

EXAMPLE 39

2,3-dihydro-7-(p-tosyloxy)-2-[[1-(phenylmethyl)-4-piperidinyl]methyl]-1H-pyrrolo]1,2-a]indol-1-one was prepared starting from the title compound of Example 26. $^1$HNMR (CDCl$_3$)δ 1.2–1.7 (m, 6H), 1.8–2.0 (m, 3H), 2.37 (s, 3H), 2.75–2.9 (m, 2H), 3.1–3.3 (m, 1H), 3.42 (s, 2H), 3.92 (dd, 1H), 4.5 (dd, 1H), 6.8 (s, 1H), 6.95 (dd, 1H), 7.1–7.3 (m, 9H), 7.6 (d, 2H) ppm.

EXAMPLE 40

2,3-dihydro-9-methyl-2-[[-(phenylmethyl)-4-piperidinyl]methyl]-1H-pyrrolo[1,2-a]indol-1-one was prepared starting from the title compound of Example 27.$^1$HNMR (CDCl$_3$) δ 1.2–1.8 (m, 6H), 1.9–2.1 (m, 3H), 2.55 (s, 3H), 2.85–2.95 (m, 2H), 3.15–3.3 (m, 1H), 3.5 (s, 2H), 3.95 (dd, 1H), 4.5 (dd, 1H), 7.15 (dd, 1H), 7.25–7.4 (m, 7H), 7.7 (d, 1H) ppm.

EXAMPLE 41

2,3-dihydro-2-methyl-7-methoxy-2-[[1-(phenylmethyl)-4-piperidinyl]methyl]-1H-pyrrolo[1,2-a]indol-1-one A solution of 2,3-dihydro-7-methoxy-2-[[1-(phenylmethyl)-4-piperidinyl]methyl]-1H-pyrrolo[1,2-a]indol-1-one (137 mg, 0.353 mmol) in dry THF (5 ml) was treated with NaH (35 mg, 0.875 mmol) at r.t. After 5 minutes, an excess of methyl iodide (0.1 ml) was added and the mixture was stirred at r.t. for 3 hours. The mixture was quenched with water and extracted with chloroform. The organic layer was dried and concentrated to give 140 mg of material which was purified through silica gel to give the title compound. $^1$HNMR (CDCl$_3$)δ 1.36 (s, 3H), 1.6–2.2 (m, 7H), 2.4–2.7 (m, 2H), 3.2–3.4 (m, 2H), 3.8 (s, 3H), 4.05 (s, 2H), 4.18 (ABq, 2H), 6.9 (s, 1H), 7.0–7.1 (m, 2H), 7.2–7.3 (m, 1H), 7.3–7.4 (m, 3H), 7.4–7.6 (m, 2H) ppm.

EXAMPLE 42

1,2,3,4-tetrahydro-2-[[1-(phenylmethyl)-4-piperidinyl]methylene]cyclopent[b]indol-1-one To a mixture of 1,2,3,4-tetrahydrocyclopent[b]-indol-1-one (440 mg, 2.6 mmol) and 1-benzylpiperidine-4-carboxaldehyde (581 mg, 2.86 mmol) in 90 ml dry THF was added 5.4 mmol of lithium diisopropylamide at −78° C. The mixture was stirred at −78° C. for 30 minutes, then warmed up to 0° C. for 1.5 hours, and then to r.t. for 15 minutes. Acetic anhydride (0.265 g, 2.6 mmol) was added, the mixture was stirred at r.t. for 1.5 hours and quenched ammonium chloride, water and extracted with chloroform. The organic layer was dried, concentrated, and purified through silica gel to give the title compound. $^1$HNMR (CDCl$_3$)δ 1.45–1.7 (m, 3H), 1.8–2.3 (m, 4H), 2.8–3.0 (m, 2H), 3.46 (s, 2H), 3.55 (s, 2H), 6.5 (m, 1H), 7.1–7.4 (m, 8H), 7.9 (m, 1H), 9.2 (s, 1H) ppm.

EXAMPLE 43

1,2,3,4tetrahydro-2-[[1-(phenylmethyl)-4-piperidinyl]methyl]cyclopent[b]indol-1-one the title compound of Example 42 (176 mg, 0.5 mmol) was dissolved in a mixture solvents of ethyl acetate (31 ml) and ethanol (31 ml) and treated with PtO2 (23 mg) and hydrogenated at 35 psi at r.t. for 2 hours. The mixture was filtered through diatomaceous earth (Celite (trademark)) and the filtrate was concentrated to give compound the title compound as off-white solid. $^1$HNMR (CDCl$_3$)δ 1.3–1.65 (m, 4H), 1.65–1.8 (m, 2H), 1.9–2.1 (m, 3H), 2.65 (dd, 1H), 2.9–3.1 (m, 3H), 3.2 (dd, 1H), 3.55 (s, 2H), 7.15–7.4 (m, 8H), 7.9 (dd, 1H), 9.15 (s, 1H) ppm.

EXAMPLE 44

1,2,3,4-tetrahydro-2-[[(phenylmethyl)-4-piperidinyl]-methylene]clopent[b]indol-3-one A solution of lithium diisopropylamide (10.64 mmol) in dry THF was cooled to −78° C. and to it was added 1,2,3,4-tetrahydrocyclopent[b]indolo-3-one (0.91 g, 5.32 mmol). The mixture was stirred at −78° C. for 30 minutes, then treated with 1-benzylpiperidine-4-carboxylaldehyde (1.29 g, 6.35 mmol) at −78° C. The mixture was warmed to r.t. for 4 hours, quenched with sodium bicarbonate, and extracted with ethyl acetate. The organic layer was dried, concentrated, and recrystallized from a mixture of ethyl acetate and ethanol to give the title compound. $^1$HNMR (CDCl$_3$)δ 1.63–1.74 (m, 3H), 2.07 (dt, 2H), 2,35–2.55 (m, 1H), 2.95 (brd, 2H), 3.54 (s, 2H), 3.65 (s, 2H), 6.63 (d, 1H), 7.19 (t, 1H), 7.25–7.33 (m, 5H), 7.40 (dt, 1H), 7.51 (d, 1H), 7.69 (d, 1H), 9.51 (s, 1H) ppm.

EXAMPLE 45

1,2,3-tetrahydro-6-methoxy-2-[[1-phenylmethyl)-4-piperidinyl]methyene]cyclopent[b]indol-3 -one The title compound was prepared by a method analogous to that of Example of 44, starting from 6-methoxy-1,2,3,4-tetrahydrocyclopent[b]indol-3-one. $^1$HNMR (CDCl$_3$)δ 1.61–1.72 (m, 4H), 2.06 (dt, 2H), 2,36–2.40 (m, 1H), 2.91–2.95 (m, 2H), 3.53 (s, 2H), 3.60 (d, 2H), 3.88 (s, 3H), 6.57 (d, 1H), 6.83 (dd, 1H), 6.88 (d, 1H), 7.26–7.33 (m, 5H), 7.55 (d, 1H), 9.04 (s, 1H) ppm.

EXAMPLE 46

1,2,34-tetrahydro-8-methoxy-2-[[1-(phenymethyl)-4-piperidinyl]methylene]-cyclopent[b]indol-3 -one The title compound was prepared by a method analagous to that described in Example 44, starting from 4-methoxy-1,2,3,8-tetrahydrocyclopent[b]indol-1-one. $^1$HNMR (DMSO-d$_6$)δ 1.42–1.53 (m, 2H), 1.66–1.69 (m, 2H), 2.04 (t, 2H), 2,38–2.5 (m, 1H), 2.81–2.85 (m, 2H), 3.48 (s, 2H), 3.70 (s, 2H), 3.90 (s, 3H), 6.35 (d, 1H), 6.58 (d, 1H), 6.99 (d, 1H), 7.24–7.34 (m, 6H), 11.8 (s, 1H) ppm.

EXAMPLE 47

1,2,3,4-tetrahydro-2-[[1-phenylmethyl)-4-piperidinyl]methylene]cyclopent[b]indol-3-one A solution of the title compound of Example 44 in a mixture of acetic acid and ethanol was treated with PtO$_2$ and hydrogenated at 45 psi for 16 hours. The mixture was filtered through diatomaceous earth (Celite (trademark)) and the filtrate was concentrated, purified through silica gel column to give the title compound. $^1$HNMR (CDCl$_3$)δ 1.35–1.55 (m, 4H), 1.68–1.80 (m, 2H), 1.93–2.70 (m, 3H), 2.75 (d, 1H), 2.90–2.95 (m, 2H), 3.05–3.09 (m, 1H), 3.30 (dd, 1H), 3.55 (s, 2H), 7.16 (t, 1H), 7.25–7.32 (m, 5H), 7.38 (t, 1H), 7.48 (d, 1H), 7.67 (d, 1H), 9.52 (brs, 1H) ppm.

EXAMPLE 48

1,2,3,4-tetrahydro-6-methoxy-2-[[1-phenylmethyl)-4-piperidinyl]methyl]cyclopent[b]indol-3-one The title compound was prepared by a method analogous to that described in Example 47 starting from the title compound of Example 45. $^1$HNMR (CDCl)δ 1.3–1.6 (m, 3H), 1.65–1.80 (m, 3H), 1.93–2.0 (m, 3H), 2.7 (dd, 1H), 2.85–2.95 (m, 2H), 3.1–3.1 (m, 1H), 3.24 (dd, 1H), 3.5 (s, 2H), 3.87 (s, 3H), 6.81 (dd, 1H), 6.86 (d, 1H), 7.23–7.31 (m, 5H), 7.53 (d, 1H), 9.07 (brs, 1H) ppm.

EXAMPLE 49

The title compound was prepared by a method analogous to that described as in Example 47 starting from the title compound of Example 46. $^1$HNMR (CDCl$_3$)δ 1.32–1.53 (m, 4H), 1.65–1.69 (m, 1H), 1.76–1.80 (m, 1H), 1.91–2.12 (m, 3H), 2.85 (dd, 1H), 2.88–2.95 (m, 2H), 3.00–3.05 (m, 1H), 3.38 (dd, 1H), 3.51 (s, 2H), 3.93 (s, 3H), 6.48 (d, 1H), 7.04 (d, 1H), 7.24–7.32 (m, 6H), 9.49 (brs, 1H) ppm.

EXAMPLE 50

1,2,3,4-tetrahydro-8-methyl-2-[[1-(phenylmethyl)-4-piperidinyl]methyl]cyclopent[b]indol-3-one A solution of 1,2,3,4-tetrahydro-2-[1-(phenylmethyl)-4-piperidinyl]methyl]-cyclopent[b]indol-1-one (350 mg, 1 mmol) in dry THF was treated with 60% sodium hydride in oil (48 mg, 1.2 mmol) and MeI (1.3 mmol) at r.t. The mixture was stirred at r.t. overnight, quenched with water and extracted with ethyl acetate. The organic layer was dried and concentrated to give the title compound. $^1$HNMR (CDCl)δ 1.55–1.68 (m, 1H), 1.75–2,35 (m, 5H), 2.60–2.80 (m, 3H), 2.95–3.05 (m, 1H), 3.27 (dd, 1H), 3.35–3.57 (m, 2H), 3.86 (s, 3H), 4.15 (s, 2H), 7.15 (t, 1H), 7.34 (t, 1H), 7.37–7.44 (m, 4H), 7.62–7.65 (m, 3H) ppm.

EXAMPLE 51

2,3-dihydro-1-oxo-1H-pyrrolo[1,2-a]benzimidazole

A solution of 2,3-dihydro-1-hydroxy-1H-pyrrolo-[1,2-a]benzimidazole (1.0 g, 5.75 mmol)) in methylene chloride was treated with mangenese dioxide (5 g, 58 mmol) at r.t. and stirred for 10 hour. The mixture was diluted with ethyl acetate and filtered through diatomaceous earth (Celite (trademark)). The filtrate was concentrated and purified to give the title compound. $^1$HNMR (CDCl$_3$)δ 3.28 (t, 2H), 4.48 (t, 2H), 7.3–7.45 (m, 2H), 7.45–7.55 (m, 1H), 7.86–7.94 (m, 1H) ppm.

EXAMPLE 52

2,3-dihydro-2-[[1-(phenylmethyl)-4-piperidinyl]methylene]-1H-pyrrolo[1,2-a]benzimidazol-1-one To a solution of 2,3-dihydro-1-oxo-1H-benzimidazole (200 mg, 1.17 mmol) in dry THF was added NaH and 1-benzylpiperidine-4-carboxaldehyde (240 mg, 1.16 mmol) at 0° C. The mixture was stirred at that temperature for 30 minutes then stirred at r.t. for 1 hour. The mixture was then quenched with saturated ammonium chloride and water and then extracted with chloroform. The organic layer was dried, concentrated, and purified from silica gel to give the title compound as a yellow solid. $^1$HNMR (CDCl$_3$)δ 1.4–1.7 (m, 4H), 1.9–2.1 (m, 2H), 2.1–2.3 (m, 1H), 2.7–2.9 (m, 2H), 3.44 (s, 2H), 4.92 (ABq, 2H), 6.85 (m, 1H), 7.1–7.5 (8H), 7.85 (m, 1H) ppm.

EXAMPLE 53

2,3-dihydro-2-[[--(phenylmethyl)-4-piperidinyl]methylene]-1H-pyrrolo[1,2-a]benzimidazol-1-one A solution of the compound of Example 52 (190 mg, 0.53 mmol) in 60 ml of a 1:1 mixture of THF and ethanol was treated with PtO$_2$ (20 mg) and hydrogenated at 45 psi at r.t. for 30 minutes. The mixture was filtered through diatomaceous earth (Celite (trademark)) and the filtrate was concentrated to give a tan solid. The tan solid was purified through silica gel to give compound. $^1$HNMR (CDCl$_3$) δ 1.3–2.2 (m, 9H), 2.7–2.9 (m, 2H), 3.3–3.4 (m, 1H), 3.5 (s, 2H), 4.1 (dd, 1H), 4.7 (dd, 1H), 7.2–7.6 (m, 8H), 8.0 (m, 1H) ppm.

EXAMPLE 54

2,3-dihydro-7-methoxy-2-[[1-(phenylmethyl)-4-piperidinyl]methyl]-1H-pyrrolo[1,2-a[indol-1-ol To a solution of 2,3-dihydro-7-methoxy-2-[[1-(phenylmethyl)-4-piperidinyl]methyl]-1H-pyrrolo[1-,2a]indol-1-one (200 mg, 0.515 mmol) in EtOH (10 ml) was treated with sodium borohydride (22.5 mg, 0,595 mmol) at r.t. After 30 minutes, the mixture was heated to reflux for hour, quenched with water and extracted with methylene chloride. The organic layer was dried and concentrated to give 180 mg of a mixture of diasteromers of the title compound as a white solid. $^1$HNMR (CDCl)δ 1.2–2.2 (m, 10H), 2.8–3.0 (m, 2H), 3.5 (2 sets of s, 2H), 3.55–3.8 (m, 1H), 3.8 (s, 3H), 4.1 (dd, 0.6H), 4.35 (dd, 0.4H), 4.9 (d, 0.6H), 5.05 (d, 0.4H), 6.25 (s, 0.6H), 6.3 (s, 0.4H), 6.85 (m, 1H), 7.1 (m, 1H), 7.15 (m, 1H), 7.2–7.4 (m, 5H) ppm.

EXAMPLE 55

2,3-dihydro-1-acetoxy-7-methoxy-2-[[1-(phenylmethyl)-4-piperidinyl]methyl]-1H-pyrrolo[1,2-a]indole A solution of the title compound of Example 54 (210 mg, 0.54 mmol) in 10 ml of methylene chloride was treated with acetic anhydride (83 mg, 0.81 mmol) and pyridine (72 mg, 0.91 mmol) and stirred at r.t. for 5 hour. The mixture was quenched with water and the organic layer was separated, dried and concentrated to give 219 mg of yellow oil which was purified through silica gel column chromatography to give the title compound as a yellow oil. $^1$HNMR (CDCl$_3$)$\delta$ 1.2-2.0 (m, 9H), 2.0 (s, 0.4H), 2.05 (s, 0.6H), 2.8-2.9 (m, 2H), 2.9-3.1 (m, 1H), 3.59 (m, 2H), 3.65-3.8 (m, 1H), 3.85 (s, 3H), 4.2 (dd, 0.4H), 4.35 (dd, 0.6H), 5.8 (d, 0.6H), 6.05 (d, 0.4H), 6.32 (s, 0.6H), 6.35 (s, 0.4H), 6.8 (m, 1H), 7.0 (m, 1H), 7.2-7.4 (m, 5H) ppm.

EXAMPLE 56

2,3-dihydro-1-methyl-2-[[1-(phenylethyl)-4-piperidinyl]methyl]-1H-pyrrolo[1,2-a]indol-1-ene To a solution of methylmagnesium bromide (5.16 mol) in 25 ml of dry tetrahydrofuran was added a solution of 2,3-dihydro-7-methoxy-2-[[1-(phenylmethyl)-4-piperidinyl]methyl]-1H-pyrrolo[1,2-a]indol-1-one (1 g, 2.58 mmol) in dry THF (25 ml) at 0° C. The mixture was stirred at that temperature for 2 hours and then warmed to r.t., quenched with 1N HCl to pH 1 and extracted with chloroform. The organic layer was washed with saturated sodium bicarbonate and brine, dried and concentrated to give the crude material which was purified through silica gel to give the title compound. $^1$HNMR (CDCl$_3$)$\delta$ 1.45-2.0 (m, 5H), 2.0 (s, 3H), 2.3-2.6 (m, 4H), 3.25 (m, 2H), 3.7 (s, 2H), 3.8 (s, 2H), 3.9 (s, 2H), 6.74 (s, 1H), 6.76 (dd, 1H), 6.94 (s, 1H), 7.02 (d, 1H), 7.3-7.6 (m, 5H) ppm. $^{13}$NMR (CDCl$_3$) 9.7, 28.4, 29.9, 32.2, 36.0, 52.8, 55.8, 61.4, 107.5, 109.1, 111.8, 112.8, 124.7, 128.9, 129.1, 130.8, 132.2, 135.0, 135.8, 55.7 ppm.

EXAMPLE 57

2,3-dihydro-7-methoxy-2-[[1-(phenylmethyl)-4-piperidinyl]methyl]-1H-pyrrolo[1,2-a]indol-1-oxime A solution of 2,3-dihydro-7-methoxy-2-[[1-(phenylmethyl)-4-piperidinyl]methyl]-1H-pyrrolo[1,2-a]indol-1-one (100 mg, 0.26 mmol) in EtOH (25 ml) and water (25 ml) was treated with hydroxylamine hydrochloride (54 mg) and sodium acetate (105 mg) at r.t. The mixture was refluxed for 24 hours, cooled to r.t. and the ethanol was removed. The residue was washed with water and extracted with chloroform. The organic layer was dried and concentrated to give a yellow solid. The yellow solid was purified through silica gel column to give the title compound as a mixture of diasteromers. $^1$HNMR (CDCl$_3$)$\delta$ 1.4-2.1 (m, 9H), 2.9-3.1 (m, 2H), 3.5-3.7 (m, 3H), 3.95 (s, 3H), 4.25-4.45 (m, 1H), 6.8-7.0 (m, 2H), 7.0-7.2 (m, 2H), 7.2-7.4 (m, 5H) ppm.

EXAMPLE 58

2,3-dihydro-6-methoxy-2-[[1-(phenylmethyl)-4-piperidinyl]methylene-1H-cyclopent[b]benzofuran-1-one The title compound was prepared by a method analogous to that described in Example 44, starting from 2,3-dihydro-6-methoxy-1H-cyclopent[b]benzofuran-1-one. A 79% yield of the title compound was obtained as a pale yellow solid. The material was recrystallized from ethyl acetate to give pale yellow needles, mp. 200°-201° C.; Anal. Calc. for CH$_{25}$H$_{25}$NO$_3$: C, 77.49; H, 6.50; N, 3.61; Found C, 77.33; H, 6.51; N, 3.64.

EXAMPLE 59

1,2,3,4-tetrahydro-6-methoxy-2-[[1-(t-butoxycarbonyl-4-piperidinyl]methylene]cyclopent[b]indol-3-one The title compound was prepared by a method analogous to that described in Example 44, starting from 6-methoxy-1,2,3,4-tetrahydrocyclopent[b]indol-3-one and 1-(t-butoxycarbonyl)piperidine-4-carboxaldehyde, mp. 235°-236° C. (dec.); Anal. Calc. for C$_{23}$H$_{28}$N$_2$O$_4$: C, 69.68; H, 7.12; N, 7.07; Found: C, 69.67; H, 6.90; N, 6.98.

EXAMPLE 60

1,2,3,4-tetrahydro-6-methoxy-2-[[1-(t-butoxycarbonyl)-4-piperidinyl]methyl]cyclopent[b]indol-3-one PtO$_2$ (80 mg, 0.31 mmol) was added to a solution of the title compound of Example 59 (610 mg, 1.54 mmol) in 1:1 THF/EtOH (tetrahydrofuran/ethanol). The resulting mixture was hydrogenated at 50 psi for 7 hours. The reaction mixture was filtered through diatomaceous earth (Celite (trademark)). The filtrate was concentrated and the residue obtained was purified by chromatography to give the title compound (550 mg, 90%) as a pale yellow solid. Recrystallization from ethyl acetate/hexane of the material gave a white solid, mp. 192°-193° C.; Anal. Calc. for C$_{23}$H$_{30}$N$_2$O$_4$: C, 69.32; H, 7.59; N, 7.03; found: C, 69.40; H, 7.39; N, 7.02.

EXAMPLE 61

1,2,3,4-tetrahydro-6-methoxy-2-[[1-(t-butoxycarbonyl)-4-piperidinyl]methyl]cyclopent[b]indol-3 -thione Lawesson's reagent (244 mg, 0.60 mmol) was added to a mixture of the title compound of Example 60 (400 mg, 1.01 mmol) in toluene and the resulting mixture was heated to 80° C. for 15 minutes. The reaction mixture was concentrated and the residue was purified by chromatography to give the title compound (280 mg, 67%) as an orange solid. Recrystallization from ethyl acetate gave orange crystals, mp. 188°-189° C.; Anal. Calc. for C$_{23}$H$_{30}$N$_2$O$_3$S: C, 66.64; H, 7.29; N, 6.76; Found: C, 66.42; H, 7.17; N, 6.59.

EXAMPLE 62

1,2,3,4-tetrahydro-6-methoxy-2-[[1-(phenylmethyl)-4-piperidinyl]methyl]cyclopent[b]indol-3-thione Trifluoroacetic acid (7.5 ml) was added to a solution of the title compound of the Example 61 (200 mg, 0.483 mmol) and thioanisole (0.85 ml, 7.25 mmol) in methylene chloride at 0° C. After 1.5 hours, the mixture was concentrated and the residue dissolved in ethyl acetate. The organic layer was washed with 1N sodium hydroxide and brine, dried, and concentrated. The crude residue was dissolved in methylene chloride and triethylamine (0.162 ml, 1.16 mmol), followed by addition of benzyl bromide (0.069 ml, 0.58 mmol). The resulting mixture was stirred at room temperature for 24 hours. The reaction mixture was washed with saturated sodium bicarbonate, dried, and concentrated. The residue was purified by silica gel column chromatography to give the title compound (140 mg) as an orange solid. Recrystallization from ethyl acetate gave orange crystals, mp. 180°-181° C.; Anal. Calc. for C$_{25}$H$_{28}$N$_2$OS.0.5-

H₂O: C, 72.60; H, 7.07; N, 6.77; Found: C 72.72; H, 6.88; N, 6.63.

EXAMPLE 63

6,7-dihydro-6-[[-(phenylmethyl)-4-piperidinyl]methyene]-5H-thieno[3,2-b]pyrrolizine-5-one The title compound was prepared by a method analogous to that described in Example 15, starting from 2,3-dihydro-1 H-pyrrolo[1,2a](thieno[2,3-b]pyrrol)-1-one and 1-benzylpiperidine-4-carboxaldehyde. ¹H NMR (CDCl₃)δ 1.54 (m, 4H), 1.96–2.1 (m, 2H), 2.1–2.3 (m, 1H), 2.85–3.0 (m, 2H), 3.52 (s,2H), 4.9 (d,2H), 6.65 (m, 1H), 6.9–7.1 (m, 2H), 7.2 7.4 (m, 5H) ppm.

EXAMPLE 64

6,7-dihydro-6-[[(phenylmethyl)-4-piperidinyl]methyl]-5H-thieno[3,2-b]-pyrrolizine-5-one The title compound was prepared by hydrogenation of the title compound in Example 63 by a method analogous to that described in Example 28. ¹H NMR (CDCl₃)δ 1.3–2.2 (m,9H), 2.9 (m, 2H), 3.15–3.35 (m, 1H), 3.5 (s,2H), 3.95 (mm, 1H), 4.5 (dd,1H), 6.9 (s,1H), 7.0 (ABq,2H), 7.3–7.4 (m,5H) ppm.

EXAMPLE 65

2,3-dihydro-7-methoxy-2-[[1(phenylmethyl)-4-piperidinyl]methylene]-1H-pyrrolo[1,2-a](6-azaindol)-1-one The title compound was prepared by a method analogous to that described in example 15, starting from 2,3-dihydro-7-methoxy-1H-pyrrolo[1,2-a](6-azaindol)-1-one and 1-benzylpiperidine-4-carboxaldehyde. ¹H NMR (CDCl₃)δ 1.5–2.35 (m, 7H), 2.9 (m,2H), 3.5 (s,2H), 3.9 (s,3H), 4.98 (d,2H), 6.75 (m, 1H), 6.82 (s,1H), 6.92 (s,1H), 7.2–7.3 (m,5H), 8.5 (s, 1H) ppm.

EXAMPLE 66 ethyl 3-[[1-phenylmethyl)-4-piperidinyl]ethylamino]methyl-6-methylindole-2-carboxylate A mixture of ethyl 3-formyl-6-methylindol-2-carboxylate (2.0 g, 8.7 mmol) and 1-benzylpiperidine-4-ethylamine was dissolved in 1:1 ethanol/THF and treated with anhydrous sodium acetate, anhydrous sodium sulfate, and sodium cyanoborohydride. The mixture was stirred at room temperature overnight. The mixture was filtered. The filtrate was concentrated to dryness. The residue was diluted with water and extracted with ethyl acetate. The organic layer was separated, dried, and concentrated to give a yellow oil. The oil was purified through silica gel column chromatography to give the title compound as a yellow oil, ¹H NMR (CDCl₃)δ 1.1–1.35 (m,2H), 1.4 (t,3H), 1.5–1.8 (m,5H), 1.8–2.0 (m,2H), 2.45 (s,3H), 2.6 (t,2H), 2.8 (m,2H), 3.44 (s,2H), 4.2 (s,2H), 4.4 (q,2H), 6.96 (d,1H), 7.14 (s,1H), 7.2–7.35 (m,5H), 7.6 (d,1H), 8.62 (brs,1H) ppm.

EXAMPLE 67 ethyl 3-[[1-phenylmethyl)-4-piperidinyl]ethylamino]methyl-5-methyl-indole-2-carboxylate The title compound was prepared by the method analogous to that described in Example 66, starting from ethyl 3-formyl-5-methyl-indole-2-carboxylate. ¹H NMR (CDCl₃)δ 1.42 (t,3H), 1.3–1.6 (m,2H), 1.6–1.8 (m,5H), 2.4 (s,3H), 2.5–2.7 (m,2H), 3.0 (t,2H), 3.05–3.2 (m,2H), 3.85 (s,2H), 4.3–4.6 (m,4H), 7.15 (d, 1H), 7.24 (s,1H), 7.3–7.5 (m,5H), 7.53 (s, 1H), 9.85 (brs, 1H) ppm.

EXAMPLE 68 ethyl 3-[[1-phenylmethyl)-4-piperidinyl]ethylamino]methyl-6-methoxyindole-2-carboxylate The title compound was prepared by the method analogous to that described in Example 66, starting from ethyl 3-formyl-6-methoxyindole-2-carboxylate. ¹H NMR (CDCl)δ 1.1–1.7 (m,7H), 1.36 (t,3H), 1.8–2.0 (m,2H), 2.67 (t,2H), 2.80 (m,2H), 3.44 (s,2H), 3.78 (s,3H), 4.15 (s,2H), 4.32 (q,2H), 6.7–6.8 (m,2H), 7.1–7.3 (m,5H), 7.5 (d,1H) ppm.

EXAMPLE 69

3-[[1-phenylmethyl)-4-piperidinyl]ethylamino]methyl-6-methyl-indole-2-carboxylic acid A solution of the title compound of Example 66 (521 mg, 1.2 mmol) in 5 ml of dioxane was treated with 2.0 ml of 0.5 M aqueous lithium hydroxide at room temperature. The mixture was stirred at room temperature overnight and quenched with 0.9 ml of 2.2N HCl gas in dioxane and concentrated to dryness. The residue was diluted with water and extracted twice with chloroform. The organic layer was dried and concentrated to give the title compound as an oil, ¹H NMR (CD₃OD)δ 1.35–1.5 (m,3H), 1.6–1.7 (m,4H), 1.8–1.95 (m,2H), 2.4 (s,3H), 2.8 (dt,2H), 3.05 (t,2H), 4.1 (s,2H), 4.4 (s,2H), 6.95 (d, 1H), 7.2 (s,1H), 7.35–7.5 (m,5H), 7.52 (d, 1H) ppm.

EXAMPLE 70

3-[[1-phenylmethyl)-4-piperidinylamino]methyl-5-methyl-indole-2-carboxylic acid

The title compound was prepared by hydrolysis of ethyl 3-[[1-(phenylmethyl)-4-piperidinyl]ethylamino]-methyl-5- methyl-indole-2-carboxylate by the method analogous to that described in Example 69. ¹H NMR (CD₃OD)δ 1.35–2.0 (m, 9H), 2.4 (s, 3H), 2.9–3.15 (m, 1H), 3.45 (m,2H), 4.28 (s,2H), 4.45 (s,2H), 7.1 (d,1H), 7.35 (d,1H), 7.45–7.6 (m,6H) ppm.

EXAMPLE 71

3-[[phenylmethyl)-4-piperidinyl]ethylamino]methyl-6-methoxyindole-2-carboxylic acid The title compound was prepared by hydrolysis of ethyl 3-[[1-(phenylmethyl)-4 -piperidinyl]ethylamino]-methyl-6-methoxy-indole-2-carboxylate by the method analogous to that described in Example 69. ¹H NMR (CD₃OD)δ 1.4–1.55 (m, 2H), 1.65–1.8 (m, 3H), 1.8–1.9 (m, 2H), 2.85–2.95 (m, 2H), 3.08 (t,2H), 3.8 (s,3H), 4.2 (s,2H), 4.4 (s,2H), 6.75 (dd, 1H), 6.9 (d,1H), 7.4–7.6 (m,6H) ppm.

EXAMPLE 72

1,2,3,4-tetrahydro-6-methyl-2-[2-[1-(phenylmethyl)-4-piperidinyl]ethyl]pyrrolo[3,4-[b]indol-3-one A solution of 3-[[1-(phenylmethyl)-4-piperidinyl]ethylamino]methyl-6-methyl-indole-2-carboxylic acid (330 mg, 0.815 mmol) in DMF (4 ml) was treated with dimethylaminopyridine (20 mg, 0.163 mmol), 4-methylmorpholine (83 mg, 0.815 mmol) and 1-(3-dimethylaminopropyl)-3-ethyl carbodimide hydrochloride (192 mg, 1 mmol) and stirred at room temperature for 19 hours. The mixture was treated with ethyl acetate and washed with sodium bicarbonate. The organic layer was washed with brine, dried, and concentrated to give the crude product. The crude material was triturated with ethyl/acetate to give the title compound as a pale yellow solid. Recrystallization from ethyl acetate gave a pale yellow solid, mp. 189°–191° C.; Anal. Calc. for $C_{25}H_{29}N_3O.0.3H_2O$: C, 76.41; H, 7.59; N, 10.69; Found: C, 76.12; H, 7.23; N, 10.53.

EXAMPLE 73

1,2,3,4-tetrahydro-7-methyl-2-[[2-[-1(phenymethyl)-4-piperidinyl]ethyl]pyrrolo[3,4-b]indol-3-one The title compound was prepared by the method analogous to that described in Example 72, starting from 3-[[1-(phenylmethyl)-4-piperidinyl]ethylamino]-methyl-5-methyl-indole-2-carboxylic acid. Anal. Calc. for $C_{24}H_{29}N_3O$: C, 76.76; H, 7.78; N, 11.19; Found: C, 76.80; H, 7.44; N, 10.72.

EXAMPLE 74

1,2,3,4-tetrahydro-6-methoxy-2-[2-[1-(phenylmethyl)-4-piperidinyl]ethyl]-pyrrolo[3,4-bindol-3-one The title compound was prepared by the method analogous to that described in Example 72, starting from 3-[[1-(phenylmethyl)-4-piperidinyl]ethylamino]-methyl-6-methoxy-indole-2-carboxylic acid. $^1$H NMR $(CDCl_3)\delta$ 1.2–1.4 (m,3H), 1.55–1.68 (m, 2H), 1.68–1.84 (m, 2H), 1.84–2.0 (m, 2H), 2.85 (m,2H), 3.44 (s,2H), 3.64 (5,2H), 3.82 (s,3H), 34.36 (s,2H), 6.8 (dd,1H), 6.95 (d, 1H), 7.16–7.3 (m,5H), 7.42 (d,1H) ppm.

EXAMPLE 75

2,3-dihydro-7-hydroxy-2-[[1-(phenylmethyl)-4-piperidinyl]methyl]-1H-pyrrolo[1,2-a]indol-1one A solution of 2,3-dihydro-7-methoxy-2-[[1-(phenylmethyl)-4-piperidinyl]methyl]-1H-pyrrolo[1,2-a]indol-1-one (1.599 g, 4.12 mmol) in 95 ml of methylene chloride was treated with potassium carbonate (5.696 g, 41.2 mmol) and cooled to $-78°$ C. Boron tribromide $(BBr_3)$ was added dropwise to the cooled solution. After addition, the resulting solution was stirred at 0° C. for one hour, then at room temperature overnight. The mixture was treated with 36 g of potassium carbonate and 100 ml of water and stirred for one hour. The organic layer was separated, washed with water, dried and concentrated to give 1.652 g of yellow solid which was purified through silica gel column chromatography to give 0.988 g of the title compound. This material was recrystallized from ethyl acetate to give brown crystals, mp. 186°–188° C. Anal. Calc. for $C_{24}H_{26}N_2O_2.0.1H_2O$: C, 76.60; H, 7.02; N, 7.45; Found C, 76.45; H, 7.18; N, 7.38.

EXAMPLE 76

2,3-dihydro-7-acetoxy-2-[[1-(phenylmethyl)-4-piperidinyl]methyl]-H-pyrrolo[1,2-a]indol-1-one A solution of 2,3-dihydro-7-hydroxy-2-[[1-(phenylmethyl)-4-piperidinyl]methyl]-1H-pyrrolo[1,2-a]indol-1-one (255 mg, 0.68 mmol) in 25 ml of methylene chloride was treated with acetic anhydride (83 mg, 0.81 mmol) and triethyl amine (93 mg, 0.91 mmol) and stirred at room temperature overnight. The mixture was quenched with water and the organic layer was separated, dried, and concentrated to give 244 mg of title compound as an off-white solid. The solid was recrystallized from ethyl acetate to give white powder, mp. 140.5°–141.5° C. ; Anal. Calc. for $C_{26}H_{28}N_2O_3$: C, 74.97; H, 6.78; N, 6.73; Found: C, 74.70; H, 6.72; N, 6.66.

EXAMPLE 77

2,3-dihydro-1-oxo-2-[[1-(phenylmethyl)-4-piperidinyl]-methyl]-1H-pyrrolo[1,2-a]indol-7-ol, N-methyl carbamate ester A solution of 2,3-dihydro-7-hydroxy-2-[[1-(phenylmethyl)-4-piperidinyl]methyl-1H-pyrrolo[1,2-a]indol-1-one (252 mg, 0.67 mmol) in 75 ml of benzene was treated with 5 mg of sodium hydride and methyl isocyanate (0.1 ml, 1.62 mmol) and stirred at room temperature for one hour. The mixture was quenched with water and the organic layer was separated, dried and concentrated to give 232 mg of the title compound as an off-white solid. The solid was recrystallized from ethyl acetate to give a white powder, mp. 148°–150° C.; Anal. Calc. for $C_{26}H_{29}N_3O$: C, 72.36; H, 6.77; N, 9.74; Found: C, 72.41; H, 6.67; N, 9.67.

EXAMPLE 78

1,2,3,4-tetrahydro-5-methoxy-2-[[1-phenylmethyl)-4-piperidinyl]methyene]cyclopent[b]indol-3-one The title compound was prepared by a method analogous to that described in Example 44, starting from 5 methoxy-1,2,3,4-tetrahydroclopent[b]indol-3-one. m. p. 200°–201° C.; Anal. Calc. for $C_{25}H_{26}N_2O_2$: C, 75.92; H, 6.88; N, 7.08; Found: C, 76.04; H, 6.52; N, 6.96.

EXAMPLE 79

1,2,3,4tetrahydro-7-methoxy-2-[[1-phenylmethyl)-4-piperidinyl]methylene]cyclopent[b]indol-3-one The title compound was prepared by a method analogous to that described in Example 44, starting from 7-methoxy-1,2,3,4-tetrahydrocyclopent[b]indol-3-one. m. p. 239.5°–240° C.; Anal. Calc. for $C_{25}H_{26}N_2O_2.0.25$-$H_2O$: C, 76.80; H, 6.83; N, 7.16; Found: C, 76.72; H, 6.91; N, 7.01.

EXAMPLE 80

1,2,3,4-tetrahydro-6,7-dimethoxy-2-[[1-(phenylmethyl)-4-piperidinyl]methylene]cyclopent[b]indol-3-one The title compound was prepared by a method analogous to that described in Example 44, starting from 6,7-dimethoxy-1,2,3,4-tetrahydrocyclopent[b]indol-3-one. mp. 244.5°–245° C.; Anal. Calc. for $C_{26}H_{28}N_2O_3.0.5H_2O$: C, 73.39; H, 6.87; N, 6.58; Found: C, 73.65; H, 6.87; N, 6.58.

EXAMPLE 81

1,2,34-tetrahydro-6,7-dimethyl-2-[[1-(phenymethyl)-4-piperidinyl]methylene]cyclopent[b]indol-3 -one The title compound was prepared by a method analogous to that described in Example 44, starting from 6,7-dimethyl-1,2,3,4-tetrahydrocyclopent[b]indol-3-one. mp. 244°–245° C.; Anal. calc. for $C_{26}H_{28}N_2O$: C, 81.21; H, 7.34; N, 7.29; Found: C, 81.20; H, 7.19; N, 7.26.

EXAMPLE 82

1,2,3,4-tetrahydro-5-methoxy-2-[[1-(phenylmethyl)-4-piperidinyl]methyl]cyclopent[b]indol-3-one The title compound was prepared by a method analogous to that described in Example 47, starting from the title compound of Example 78, mp. 179°–180° C.; $^1$H NMR $(CDCl_3)\delta$ 1.21–1.47, 1.66–1.78 (m, 2H), 1.91–2.11

(m, 3H), 2.72 (dd, 1H), 2.89–2.95 (m, 2H), 3.04–3.06 (m, 1H), 3.25 (dd, 1H), 3.51 (s, 2H), 3.94 (s, 3H), 6.78 (d, 1H), 7.08 (t,1H), 7.22–7.31 (m, 6H), 8.87 (s, 1H) ppm.

EXAMPLE 83

1,2,3,4-tetrahydro-7-methoxy-2-[[1-(phenylmethyl)-4-piperidinyl]methyl]cyclopent[b]indol-3-one The title compound was prepared by a method analogous to that described in Example 47, starting from, the title compound of Example 80, mp. 213°–214° C.; Anal. Calc. for $C_{26}H_{28}N_2O_2$: C, 77.29; H, 7.26; N, 7.21; Found: C, 76.73; H, 7.19; N, 7.26.

EXAMPLE 84

1,2,3,4-tetrahydro-6,7-methoxy-2-[[1-(phenylmethyl)-4-piperidinyl]methyl]cyclopent[b]indol-3-one The title compound was prepared by a method analogous to that described in Example 47, starting from the title compound of Example 80, mp. 215.5°–216.5° C.; Anal. Calc. for $C_{26}H_{30}N_2O_3$: C, 74.61; H, 7.22; N, 6.69; Found: C, 74.42; H, 7.19; N, 6.66.

EXAMPLE 85

1,2,3,4-tetrahydro-6,7-methoxy-2-[[1-(phenylmethyl)-4-piperidinyl]methyl]cyclopent[b]indol-3-one The title compound was prepared by a method analogous to that described in Example 47, starting from the title compound of Example 81, mp. 191°–192° C.; $^1$H NMR (CDCl$_3$)δ 1.38–1.54 (m, 4H), 1.68–1.80 (m, 2H), 1.93–2.05 (m, 3H), 2.35 (s, 3H), 2.70 (d, 1H), 2.87–2.94 (m, 2H), 3.05–3.08 (m, 1H), 3.25 (dd, 1H), 3.52 (s, 2H), 7.20–7.33 (m, 6H), 7.41 (s, 1H), 9.56 (s, 1H) ppm.

EXAMPLE 86

1,2,3,4-tetrahydro-6-hydroxy-2-[[1-(phenylmethyl)-4-piperidinyl]methyl]cyclopent[b]indol-3-one A mixture of 1,2,3,4-tetrahydro-6-methoxy-2-[[1-(phenylmethyl)-4-piperidinyl]methyl]cyclopent[b]indol-3-one (200 mg, 0.51 mmol) and 48% HBr (30 ml) was heated to 110° C. for 3.5 hours. The reaction mixture was allowed to cool and saturated sodium bicarbonate was added until pH 8. The mixture obtained was filtered and the aqueous filrate was extracted with ethanol and the resulting mixture was filtered. Aqueous Na$_2$S$_2$O$_4$ was added to the ethanolic filtrate and the light brown solution obtained was concentrated. The residue was partitioned between water and boiling ethyl acetate. The organic layer was combined and washed with water, brine, dried, filtered and concentrated. The residue was purified through silica gel column chromatography to give the title compound as a yellow solid (100 mg). The material was recrystallized from ethanol to give a pale yellow solid, mp. 250°–252° C.; Anal. Calc. for $C_{24}H_{26}N_2O_2.0.25H_2O$: C, 76.06; H, 7.05; N, 7.39; ound: C, 76.27; H, 6.67; N, 7.36.

EXAMPLE 87

2,3-dihydro-6-methoxy-2-[[1-(phenylmethyl)-4-piperidinyl]methyl]cyclopent[b]benzofuran-1-one A mixture of 10% pd/c (110 mg., 0.104 mmol) and the title compound of Example 58 in 1% conc. HCL/EtOH (v/v, 70 ml) was hydrogenated in Parr Shaker at 50 psi for 11 hours. The reaction mixture was filtered through a Celite (trademark) pad. The filtrate was concentrated and the residue obtained was dissolved in EtoAC. The organic layer was washed with 10% NaOH, brine, dried, filtered, and concentrated. The residue was purified by silica gel chromatography (25% MeOH in CH$_2$Cl$_2$) to give the title compound (260 mg, 64%) as an off-white solid. Recrystallization (ZtoAC-hexane) of a sample gave a white solid, mp. 137°–138° C.; Anal. Calc. for $C_{25}H_{27}NO_3\frac{1}{4}$ H$_2$O: C 76.21; H, 7.03; N, 3.55; Found: C, 74.42; H, 7.19; N, 6.66.

EXAMPLE 88

1,2,3,8-tetrahydro-cyopent[a]indene-1-one

A solution of 3-indenepropionic acid (1.11 g, 5.9 mmol) in 100 ml of benzene was treated with PCl$_5$ (1.390 g, 6.67 mmol) and the mixture was stirred at room temperature for 2.5 hr. The reaction mixture was cooled at 0° C. and treated with a solution of stannic chloride (4.452 g, 3.97 mmol) in 50 ml of benzene. The resulting mixture was stirred at room temperature overnight and poured over cold dilure HCl and extrated with chloroform. The organic layer was washed with water, dried and concentrated to give 0.841 g (84% yield) of the title compound as a yellow solid 1H NMR (CDCl$_3$)δ 2.96(m,4H), 3.5(t,2H), 7.4(m,2H), 7.6(m,2H)ppm.

EXAMPLE 89

1,2,3,8-tetrahydro-2-[[1-phenylmethyl)-4-piperidinyl]-methylene]-cyclopent[a]indene-1-one A solution of 1,2,3,8-tetrahydro-cylcopent[a]indene-1-one (0.838 g, 4.92 mmol) in 50 ml of THF was treated with NaH (200 mg, 5 mmol) at 0° C. and stirred for 3 min. A solution of 1-benzylpiperidine-4-carboxaldehyde (1.100 g, 5.41 mmol) in 5 ml of THF was added at 0° C. After addition, the mixture was stirred at room temperature for 30 min and quenched with 10 ml of methanol, then 10 ml of water. The resulting mixture was quenched with brine and extracted with chloroform. The organic layer was dried and concentrated to column chromatography using chloroform as eluent to give the title compound as a yellow solid. The solid was recrystallized from ethanol to give crystals, mp. 141°–142° C. (decomp.). $^1$H NMR (CDCl$_3$)δ 1.5–1.8 (m, 4H), 2.1–2.3 (m, 2H), 2.8–3.1(m,6H), 3.5(s,2H), 3.6–3.8(m, 1H), 6.6(d, 1H), 7.2–7.4(m,7H), 7.5(d,1H), 7.7(d,1H)ppm.

EXAMPLE 90

1,2,3,8-tetrahydro-2-[[1-phenylmethyl)-4-piperidinyl]-methyl]cyclopent[a]indene-1-one The title compound of example 89 (456 mg, 1.28 mmol) in 75 ml of ethyl acetate was treated with PtO$_2$ (45 mg) and hydrogenated at atmospheric pressure for 5 hr. The mixture was filtered through celite and the filtrate was concentrated to give an oil which was purified through silica gel column chromatography to give the title compound as a yellow oil. $^1$H NMR (CDCl$_3$)δ 1.2–1.4 (m, 2H), 1.4–1.85(m,5H), 1.85–2.2(m,3H), 2.8–3.0(m,6H), 3.53(s,2H), 3.7–3.8(m, 1H), 7.2–7.6(m,9H) ppm.

EXAMPLE 91 ethyl 3-[[1-(phenylmethyl)-4-piperidinyl]ethylamino]methyl-5-chloro-indole-2-carboxylate The title compound was prepared by the method analogous to that described in Example 66, starting from ethyl 3-formyl-5-chloro-indole-2-carboxylate. $^1$H NMR (CDCl$_3$)δ 1.4(t,3H), 1.2–1.8(m,7H), 1.8–2.0(m,2H), 2.67(t,2H), 2.8–3.0(m,2H), 3.5(s,2H), 4.2(s,2H), 4.42(q,2H), 7.2–7.45(m,7H), 7.75 (s, 1H) ppm.

EXAMPLE 92

3-[[1-(phenylmethyl)-4-piperidinylethlamino]methyl-5-chloro-indole-2-carboxylic acid The title compound was prepared by hydrolysis of ethyl 3-[[1-(phenylmethyl)-4-piperidinyl]ethylamino]-methyl-5-chloro-indole-2-carboxylate by the method analogous to that described in Example 69. $^1$H NMR (DMSO-d$_6$)δ 1.0–1.7(m,7H), 1.8–2.0(m,2H), 2.7–3.0(m,4H), 3.4(s,2H), 4.3(s,2H), 7.1–7.4(m,7H), 7.75(s,1H) ppm.

EXAMPLE 93

1,4-dihydro-7-chloro-2-[2[-phenylmethyl)-4-piperidinyl]ethyl]pyrrolo[3,4-b]indol-3(2H)-one The title compound was prepared by the method analogous to that described in Example 72, starting from 3-[[1-phenylmethyl)-4-piperidinyl]ethylamino]-methyl-5-chloro-indole-2-carboxylic acid. Anal. calc. for C$_{24}$H$_{26}$N$_3$OCl: C, 70.66; H, 6.43; N, 10.30; found: C, 70.50; H, 6.57; N, 10.24.

EXAMPLE 94

3-[[1-(phenlmethyl)-4-piperidinyl]ethylamino]methyl-5-methyl-benzo[b]thieno-2-carboxylic acid A mixture of 3-formyl-5-methyl-benzo[b]thieno-2-carboxylic acid (1.03 g, 4.68 mmol) and 1-phenylmethyl-4-(2-aminoethyl)-piperidine (1.235 g, 5.66mmol) was dissolved in 20 ml of ethanol and 10 ml of THF. The resulting mixture was treated with anhydrous sodium acetate (1.16 g, 14.1 mmol), sodium cyanoborohydride (0.593 g, 9.44 mmol) and anhydrous sodium sulfate (3.300 g) and stirred at room temperature overnight. The reaction mixture was filtered through celite, washed with ethyl acetate. The filtrate was concentrated to dryness. The residue was dissolved in ethyl acetate and water. The organic layer was separated, washed with acid, brine, dried, filtered, and concentrated to give the title compound as a yellow solid which was used directly for the next reaction.

EXAMPLE 95

3-[[1-(phenylmethyl)-4-piperidinyl]ethylamino]methyl-6-methyl-benzo[b]thieno-2-carboxylic acid The title compound was prepared by the method analogous to that described in Example 94, starting from 3-formyl-6-methyl-benzo[b]thieno-2-carboxylic acid (1.44 g, 6.54 mmol), 1-phenylmethyl-4-(2-aminoethyl)-piperidine (1.71 g, 7.84 mmol), sodium cyanoborohydride (0.820 g, 13.08 mmol), sodium acetate (0.540 g. 6.54 mmol) and sodium sulfate in ethanol.

EXAMPLE 96

3-[[1-(phenylmethy)-4-piperidinyl]ethylamino]methyl-5-chloro-benzo[b]thieno-2-carboxylic acid The title compound was prepared by the method analogous to that described in Example 94, starting from 3-formyl-5-chloro-benzo[b]thieno-2-carboxylic acid (1.000 g, 4.54 mmol), 1-phenylmethyl-4-(2-aminoethyl)-piperidine (1.200 g, 5.50 mmol), sodium cyanoborohydride (0.570 g, 9.07 mmol), sodium acetate (0.450 g, 5.49 mmol) and sodium sulfate in 25 ml of ethanol and 5 ml of dry THF.

EXAMPLE 97

1,2-dihydro-7-methyl-2-[2-[1-phenylmethyl)-4-piperidinyl]ethyl]pyrrolo[3,4-(benzo[b]thieno)-1H-3-one A mixture of 3-[[1-(phenylmethyl)-4-piperidinyl]ethylamino]methyl-5-methyl-benzo[b]thieno-2-carboxylic acid (1.000 g, 2.37 mmol), 1-(3-dimethylaminopropyl)-3-ethylcarbodiimide hydrochloride (0.544 g, 2.84 mmol), dimethylaminopyridine (0.059 g, 0.48 mmol), and N-methylmorpholine (0.239 g, 2.36 mmol) in 12 ml of DMF was stirred at room temperature overnight. The mixture was quenched with water and extracted with ethyl acetate. The organic layer was dried, filtered, and concentrated to give 0.815 g of the crude material as a yellow oil. The yellow oil was purified through silica gel column chromatography using 10% methanol in chloroform as eluent to give the title compound as a pale oil. $^1$H NMR (CDCl$_3$)δ 1.15–1.45(m,3H), 1.5–1.8(m,4H), 1.8–2.0(m,2H), 2.47(s,3H), 2.75–2.9(m,2H), 3.45(s,2H), 3.6(t,2H), 4.4(s,2H), 7.1–7.35(m,6H), 7.5(s, 1H), 7.75(d,1H) ppm.

EXAMPLE 98

1,2-dihydro-6-methyl-2-[2-[1-(phenylmethyl)-4-piperidinyl]ethyl]pyrrolo[3,4-b](benzo[b]thieno) 1H-3-one The title compound was prepared by the method analogous to that described in Example 97, starting from 3-[[1-phenylmethyl)-4 -piperidinyl]ethylamino]-methyl-6-methylbenzo[b]thieno-2-carboxylic acid to give the title compound as a yellow glass; $^1$H NMR (CDCl$_3$)δ 1.2–1.4 (m, 3H), 1.5–1.8 (m, 4H), 1.8–2.0 (m, 2H), 2.46 (s, 3H), 1.8–2.0 (m, 2H), 3.5(s,2H), 3.6(t,2H), 4.4(s,2H), 7.1–7.4(m,6H), 7.58 (s, 1H), 7.64 (s, 1H) ppm.

EXAMPLE 99

1,2-dihydro-7-chloro-2-[2-[1-(phenylmethyl)-4-piperidinyl]ethyl]pyrrolo[3,4-benzo[b]thieno) 1H-3-one The title compound was prepared by the method analogous to that described in Example 97, starting from 3[[1-(phenylmethyl)-4-piperidinyl]ethylamino]-methyl-5-chlorobenzo[b]thieno-2-carboxylic acid to give the title compound as pale solid; $^1$H NMR (CDCl$_3$)δ 1.2–1.4(m, 3H), 1.6–1.8(m,4H), 1.8–2.05(m,2H), 2.8–3.0(m,2H), 3.5(s,2H), 3.68(t,2H), 4.5(s,2H), 7.2–7.4(m,5H), 7.42(dd, 1H), 7.74(d, 1H), 7.84(d,1H) ppm.

EXAMPLE 100

2,3-dihydro-5-methyl-1H-cyclopent[b]benzo[b]thieno)-1-one

A solution of 5-methyl-benzo[b]thieno-3-propionic acid (0.974 g, 4.43 mmol) in 100 ml of toluene was treated with PCl$_5$ (1.013 g, 4.87 mmol) and the resulting mixture was stirred at room temperature for 3 hr. The reaction mixture was cooled to 0° C. and SnCl$_4$ (3.36 g, 17.72 mmol) was added and the mixture was stirred at room temperature overnight. The mixture was quenched with dilute HCl and extracted with chloroform. The organic layer was separated, dried and concentrated to give purple solid which was triturated with di-isopropyl ether to give the tile compound as a purple crystals (615 mg). The crystals was decolorized with Darco and recystallized from ethyl acetate to give colorless crystals; mp 189.5°–190° C.; Anal. calc. for $C_{12}H_{10}SO$: C, 71.26; H, 4.98; found: C, 71.05; H, 4.72.

EXAMPLE 101

2,3-dihydro-5-methyl-2-[[1-(phenylmethyl)-4-piperidinyl]methylene]-1H-cyclopent[b](benzo[b]thieno)-1-one A solution of 2,3-dihydro-5-methyl-1H-cyclopent[b](benzo[b]thieno)-1-one (350 mg, 1.73 mmol) in 30 ml of dry THF was treated with sodium hydride (71 mg, 1.77 mmol) at 15° C. After 3 min, a solution of 1-benzyl-piperidine-4-carboxaldehyde (406 mg, 2.0 mmol) in 5 ml of dry THF was added and stirred at 15° C. for 30 min. The mixture was quenched with water and extracted with ethyl acetate. The organic layer was dried and concentrated to give a brown solid which was recrystallized from ethyl acetate to give the title compound as white crystals; mp 192°–193.5° C. (decomp.). Anal. calc. for $C_{25}H_{25}NOS$. 0.3 $H_2O$: C, 76.42; H, 6.57; N 3.56; found C, 76.30; H, 6.22; N, 3.62.

EXAMPLE 102

2,3-dihydro-5-methyl-2-[[1-phenylmethyl]-4-piperidinyl]-methyl]-1H-cyclopent[b](benzo[b]thieno)-1-one A solution of 2,3-dihydro-5-methyl-2-[[1-(phenylmethyl)-4-piperidinyl]methylene]-1H-cyclopent[b](benzo[b]thieno)-1-one (300 mg) in 100 ml of ethanol and 100 ml of ethyl acetate was treated with $PtO_2$ (30 mg) and hydrogenated at 42 psi for 1 hr (the reaction is not done). An additional $PtO_2$ (70 mg) was added and the mixture was hydrogenated for 2 hrs. The mixture was filtered through celite and the filtrate was concentrated to dryness to give 267 mg of yellow solid. The solid was purified through silica gel chromatotron using chloroform in chloroform as eluent to give 133 mg of the title compound as a white solid. The solid was recrystallized from ethyl acetate to give a colorless needle. Anal. calc. for $C_{25}H_{27}NOS$. 0.1 $H_2O$: C, 76.76; H, 6.96; N, 3.58; found: C, 76.63; H, 7.00; N, 3.78.

I claim:

1. A compound of the formula

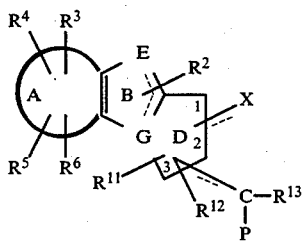

I wherein P is

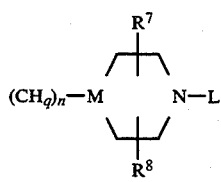

ring A is benzo, thieno, pyrido, or pyrrolo;
$R^2$ is hydrogen or ($C_1$–$C_4$) alkyl;

$R^3$, $R^4$, $R^5$ and $R^6$ are each independently selected from hydrogen, ($C_1$–$C_6$) alkoxy, benzyloxy, hydroxy, halo, ($C_1$–$C_6$)alkyl and $SO_2CH_2$-phenyl;

G is carbon or nitrogen;

E is carbon, nitrogen, oxygen, or sulfur;

the curved dashed line in ring B represents one double bond, so that ring B contains two double bonds;

each of the straight dashed lines connecting, respectively, the carbon to which P is attached and X to ring D represents an optional double bond;

the carbon at any of positions 1–3 at ring D may optionally be replaced by nitrogen when such carbon is adjacent to a carbonyl group, the carbon atom of which is at position 1, 2, or 3 of ring D, so that ring D is a lactam ring;

X is O, S, $NOR^1$ hydrogen or ($C_1$–$C_6$) alkyl with the proviso that X is double bonded to ring D only when the member of ring D to which it is bonded is carbon and X is O, S or $NOR^1$;

$R^1$ is hydrogen or ($C_1$–$C_6$) alkyl;

q is an integer from 1 to 2;

n is an integer from 1 to 3 when ring D is a lactam ring, and n is an integer from 0 to 3 when ring D is not a lactam ring;

M is carbon or nitrogen;

L is phenyl-($C_1$–$C_6$)alkyl;

$R^{11}$ is hydrogen, halo, hydroxy, ($C_1$–$C_4$) alkyl, ($C_1$–$C_4$) alkoxy or oxygen;

$R^{12}$ and $R^{13}$ are each independently selected from hydrogen, fluoro, hydroxy, acetoxy, O-mesylate, O-tosylate, ($C_1$–$C_4$)alkyl, and ($C_1$–$C_4$)alkoxy; or $R^{12}$ and $R^{13}$ may, together with the atoms to which they are attached, when both of $R^{12}$ and $R^{13}$ are attached to carbon atoms, form a three, four or five membered ring wherein each atom of said ring is carbon or oxygen;

$R^7$ and $R^8$ are each hydrogen;

or $R^8$ and $R^{12}$, together with the atoms to which they are attached, form a saturated carbocyclic ring containing 4 to 7 carbons wherein one of said carbon atoms may optionally be replaced with oxygen, nitrogen or sulfur;

with the proviso that (a) when E is carbon, nitrogen, oxygen, or sulfur, then G is carbon; (b) when G is nitrogen, then E is carbon or nitrogen; (c) when either E and G are both nitrogen, or G is carbon and E is oxygen or sulfur, then is absent; (d) each of the atoms at positions 1, 2 and 3 of ring D may be bonded by no more than one double bond; and (e) X is attached to the position on ring D that is adjacent to the position to which the hydrocarbon substituent containing P is attached;

and the pharmaceutically acceptable salts thereof.

2. A compound according to claim 1, selected from the group consisting of:

2,3-dihydro-2-[[1-(phenylmethyl)-4-piperidinyl]methylene]-1H-pyrrolo[1,2-a]indol-1-one;

2,3-dihydro-7-methoxy-2-[[1-(phenylmethyl)-4-piperidinyl]methylene]-1H-pyrrolo[1,2-a]indol-1-one;

2,3-dihydro-6,7-dimethoxy-2-[[1-(phenylmethyl)-4-piperidinyl]methylene]-1H-pyrrolo[1,2-a]indol-1-one;

2,3-dihydro-7-fluoro-2-[[1-(phenylmethyl)-4-piperidinyl]methylene]-1H-pyrrolo[1,2-a]indol-1-one;

2,3-dihydro-7-methyl-2-[[1-(phenylmethyl)-4-piperidinyl]methylene]-1H-pyrrolo[1,2-a]indol-1-one;

2,3-dihydro-6-methyl-2-[[1-(phenylmethyl)-4-piperidinyl]methylene]-1H-pyrrolo[1,2-a]indol-1-one;

2,3-dihydro-8-methyl-2-[[1-(phenylmethyl)-4-piperidinyl]methylene]-1H-pyrrolo[1,2-a]indol-1-one;

2,3-di hydro-6-methoxy-2-[[1-(phenylmethyl)-4-piperidinyl]methylene]-1H-pyrrolo[1,2-a]indol-1-one; 2,3-di hydro-7-benzyloxy-2-[[1-(phenylmethyl)-4-piperidinyl]methylene]-1H-pyrrolo[1,2-a]indol-1-one;

2,3-dihydro-7-ethoxy-2-[[1-(phenylmethyl)-4-piperidinyl]methylene]-1H-pyrrolo[1,2-a]indol-1-one;

2,3-dihydro-8-methoxy-2-[[1-(phenylmethyl)-4-piperidinyl]methylene]-1H-pyrrolo[1,2-a]indol-1-one;

2,3-dihydro-7-p-tosyloxy-2-[[1-(phenylmethyl)-4-piperidinyl]methylene]-1H-pyrrolo[1,2-a]indol-1-one;

2,3-dihydro-2-[[1-(phenylmethyl)-4-piperidinyl]methyl]-1H-pyrrolo[1,2-a]indol-1-one;

2,3-dihydro-7-methoxy-2-[[1-(phenylmethyl)-4-piperidinyl]methyl]-1H-pyrrolo[1,2-a]indol-1-one;

2,3-dihydro-7-fluoro-2-[[1-(phenylmethyl)-4-piperidinyl]methyl]-1H-pyrrolo[1,2-a]indol-1-one;

2,3-dihydro-6,7-dimethoxy-2-[[1-(phenylmethyl)-4-piperidinyl]methyl]-1H-pyrrolo[1,2-a]indol-1-one;

2,3-dihydro-9-methyl-2-[[1-(phenylmethyl)-4-piperidinyl]methyl]-1H-pyrrolo[1,2-a]indol-1-one;

2,3-dihydro-7-methyl-2-[[1-(phenylmethyl)-4-piperidinyl]methyl]-1H-pyrrolo[1,2-a]indol-1-one;

2,3-dihydro-6-methyl-2-[[1-(phenylmethyl)-4-piperidinyl]methyl]-1H-pyrrolo[1,2-a]indol-1-one;

2,3-dihydro-8-methyl-2-[[1-(phenylmethyl)-4-piperidinyl]methyl]-1H-pyrrolo[1,2-a]indol-1-one;

2,3-dihydro-6-methoxy-2-[[1-(phenylmethyl)-4-piperidinyl]methyl]-1H-pyrrolo[1,2-a]indol-1-one;

2,3-dihydro-6-benzyloxy-2-[[1-(phenylmethyl)-4-piperidinyl]methyl]-1H-pyrrolo[1,2-a]indol-1-one;

2,3-dihydro-7-ethoxy-2-[[1-(phenylmethyl)-4-piperidinyl]methyl]-1H-pyrrolo[1,2-a]indol-1-one;

2,3-dihydro-8-methoxy-2-[[1-(phenylmethyl)-4-piperidinyl]methyl]-1H-pyrrolo[1,2-a]indol-1-one;

2,3-dihydro-7-tosyloxy-2-[[1-(phenylmethyl)-4-piperidinyl]methyl]-1H-pyrrolo[1,2-a]indol-1-one;

2,3-dihydro-7-hydroxy-2-[[1-(phenylmethyl)-4-piperidinyl]methyl]-1H-pyrrolo[1,2-a]indol-1-one;

2,3-dihydro-2-methyl-7-methoxy-2-[[1-(phenylmethyl)-4-piperidinyl]methyl]-1H-pyrrolo[1,2-a]indol-1-one;

2,3-dihydro-7-acetoxy-2-[[1-(phenylmethyl)-4-piperidinyl]methyl]-1H-pyrrolo[1,2-a]indol-1-one;

2,3-dihydro-1-oxo-2-[[1-(phenylmethyl)-4-piperidinyl]methyl]-1H-pyrrolo[1,2-a]indole-7-ol, methyl carbamate ester;

2,3-dihydro-7-methoxy-2-[[1-(phenylmethyl)-4-piperidinyl]methyl]-1H-pyrrolo[1,2-a]indol-1-thione;

2,3-dihydro-7-methyl-2-[[1-(phenylmethyl)-4-piperidinyl]methyl]-1H-pyrrolo[1,2-a]indol-1-thione;

2,3-dihydro-7-hydroxy-2-[[1-(phenylmethyl)-4-piperidinyl]methyl]-1H-pyrrolo[1,2-a]indol-1-thione;

1,2,3,4-tetrahydro-2-[[1-(phenylmethyl)-4-piperidinyl]methyl-cyclopent[b]indol-1-one;

1,2,3,4-tetrahydro-2-[[1-(phenylmethyl)-4-piperidinyl]methylene]-cyclopent[b]indol-3-one;

1,2,3,4-tetrahydro-4-methyl-2-[[1-(phenylmethyl)-4-piperidinyl]methylene]-cyclopent[b]indol-3-one;

1,2,3,4-tetrahydro-5-methoxy-2-[[1-(phenylmethyl)-4-piperidinyl]methylene]-cyclopent[b]indol-3-one;

1,2,3,4-tetrahydro-6-methoxy-2-[[1-(phenylmethyl)-4-piperidinyl methylene]-cyclopent[b]indol-3-one;

1,2,3,4-tetrahydro-8-methoxy-2-[[1-(phenylmethyl)-4-piperidinyl methylene]-cyclopent[b]indol-3-one;

1,2,3,4-tetrahydro-7-methoxy-2-[[1-(phenylmethyl)-4-piperidinyl methylene]-cyclopent[b]indol-3-one;

1,2,3,4-tetrahydro-4-benzoyl-2-[[1-(phenylmethyl)-4-piperidinyl]methylene]-cyclopent[b]indol-3-one;

1,2,3,4-tetrahydro-6,7-dimethoxy-2-[[1-(phenylmethyl)-4-piperidinyl]methylene]-cyclopent[b]indol-3-one;

1,2,3,4-tetrahydro-6,7-dimethyl-2-[[1-(phenylmethyl)-4-piperidinyl]methylene]-cyclopent[b]indol-3-one;

1,2,3,4-tetrahydro-2-[[1-(phenylmethyl)-4-piperidinyl]methyl]-cyclopent[b]indol-3-one;

1,2,3,4-tetrahydro-4-methyl-2-[[1-(phenylmethyl)-4-piperidinyl]methyl]-cyclopent[b]indol-3-one;

1,2,3,4-tetrahydro-5-methoxy-2-[[1-(phenylmethyl)-4-piperidinyl]methyl]-cyclopent [b]indol-3-one;

1,2,3,4 -tetrahydro - 6 -methoxy- 2 -[[1-(phenylmethyl)-4-piperidinyl]methyl]-cyclopent [b]indo 1-3-one;

1,2,3,4-tetrahydro-8-methoxy-2-[[1-(phenylmethyl)-4-piperidinyl]methyl]-cyclopent[b]indol-3-one;

1,2,3,4-tetrahydro-4-benzyl-2-[[1-(phenylmethyl)-4-piperidinyl]methyl]-cyclopent[b]indol-3-one;

1,2,3,4-tetrahydro-7-methoxy-2-[[1-(phenylmethyl)-4-piperidinyl]methyl]-cyclopent[b]indol-3-one;

1,2,3,4-tetrahydro-4-benzoyl-2-[[1-(phenylmethyl)-4-piperidinyl]methyl]-cyclopent[b]indol-3-one;

1,2,3,4-tetrahydro-4-tosyl-2-[[1-(phenylmethyl)-4-piperidinyl]methyl]-cyclopent[b]indol-3-one;

1,2,3,4-tetrahydro-6,7-dimethoxy-2-[[1-(phenylmethyl)-4-piperidinyl]methyl]-cyclopent[b]indol-3-one;

1,2,3,4-tetrahydro-6-hydroxy-2-[[1-(phenylmethyl)-4-piperidinyl]methyl]-cyclopent[b]indol-3-one;

1,2,3,4-tetrahydro-7-hydroxy-2-[[1-(phenylmethyl)-4-piperidinyl]methyl]-cyclopent[b]indol-3-one;

1,2,3,4-tetrahydro-6,7-dimethyl-2-[[1-(phenylmethyl)-4-piperidinyl]methyl]-cyclopent[b]indol-3-one;

1,2,3,4-tetrahydro-4-methyl-2-[[1-(phenylmethyl)-4-piperidinyl]methyl]-cyclopent[b]indol-3-thione;

1,2,3,4-tetrahydro-5-methoxy-2-[[1-(phenylmethyl)-4-piperidinyl]methyl]-cyclopent[b]indol-3-thione;

1,2,3,4-tetrahydro-6-methoxy-2-[[1-(phenylmethyl)-4-piperidinyl]methyl]-cyclopent[b]indol-3-thione;

1,2,3,4-tetrahydro-8-methoxy-2-[[1-(phenylmethyl)-4-piperidinyl]methyl]-cyclopent[b]indol-3-thione;

1,2,3,4-tetrahydro-7-methoxy-2-[[1-(phenylmethyl)-4-piperidinyl]methyl]-cyclopent[b]indol-3-thione;

1,2,3,4-tetrahydro-6,7-methoxy-2-[[1-(phenylmethyl)-4-piperidinyl]methyl]-cyclopent[b]indol-3-thione;

1,2,3,4-tetrahydro-6-hydroxy-2-[[1-(phenylmethyl)-4-piperidinyl]methyl]-cyclopent[b]indol-3-thione;

1,2,3,4-tetrahydro-7-hydroxy-2-[[1-(phenylmethyl)-4-piperidinyl]methyl]-cyclopent[b]indol-3-thione;

1,2,3,4-tetrahydro-6,7-dimethyl-2-[[1-(phenylmethyl)-4-piperidinyl]methyl]-cyclopent[b]indol-3-thione;

2,3-dihydro-6-methoxy-2-[[1-(phenylmethyl)-4-piperidinyl]methylene]-1H-cyclopent[b](benzo[b]furan)-1-one;

2,3-dihydro-6-methoxy-2-[[1-(phenylmethyl)-4-piperidinyl]methyl]-1H-cyclopent[b](benzo[b]furan)-1-one;

2,3-dihydro-2-[[1-(phenylmethyl)-4-piperidinyl]methyl]-1H-pyrrolo[1,2-a]benzimidazol-1-one;

2,3-dihydro-6-methoxy-2-[[1-(phenylmethyl)-4-piperidinyl]]methylene]-1H-cyclopent[b](benzo[b]thieno)-1one;

6,7-dihydro-6-[[1-(phenylmethyl)-4-piperidinyl]methyl]-5H-thieno [3,2-b]-pyrrolizine-5-one;

2,3-dihydro-2 -[[1-(phenylmethyl)-4-piperidinyl]methyl]-1H-pyrrolo[1,2-a](thieno[2,3-b]pyrrol)-1-one;

2,3-dihydro-7-methoxy-2-[[1-(phenylmethyl)-4-piperidinyl]methylene]-1H-pyrrolo[1,2-a](6-azaindol )-1-one;

2,3-dihydro-7-methoxy-2-[[1-(phenylmethyl)-4-piperidinyl]methyl]-1H-pyrrolo[1,2-a](6-azaindol )-1-one;

1,2,3,4-tetrahydro-6-methoxy-2-[[1-(phenylmethyl)-4-piperidinyl]ethyl]-pyrrolo[3,4-b]indol-3-one;

1,2,3,4-tetrahydro-6-methyl-2-[[1-(phenylmethyl)-4-piperidinyl]ethyl]-pyrrolo[3,4-b]indol-3-one;

1,2,3,4-tetrahydro-7-methyl-2-[2-[1-(phenylmethyl)-4-piperidinyl]ethyl]-pyrrolo[3,4-b]indol-3-one;

2,3-dihydro-1-hydroxy-7-methoxy-2-[[1-(phenylmethyl)-4-piperidinyl]methylene]-1H-pyrrolo[1,2-a]indole;

2,3-dihydro-1-hydroxy-7-methoxy-2-[[1-(phenylmethyl)-4-piperidinyl]methyl]-1H-pyrrolo[1,2-a]indole;

2,3-dihydro-1-acetoxy-7-methoxy-2-[[1-(phenylmethyl)-4-piperidinyl]methyl]-1H-pyrrolo[1,2-a]indole;

2,3-dihydro-7-methoxy-2-[[1-(phenylmethyl)-4-piperidinyl]methyl]-1H-pyrrolo[1,2-a]indol-1-oxime;

1,4-dihydro-7-chloro-2-[2-1-(phenylmethyl)-4-piperidinyl]ethyl]pyrrolo[3,4-b]indol-3(2H)-one;

1,2-dihydro-7-methyl-2-[2-[1-(phenylmethyl)-4-piperidinyl]ethyl]pyrrolo[3,4-(benzo[b]thieno)-1H-3-one;

1,2-dihydro-6-methyl-2-[2-[1-(phenylmethyl)-4-piperidinyl]ethyl]pyrrolo[3,4-b](benzo[b]thieno) 1H-3-one;

1,2-dihydro-7-chloro-2-[2-[1-(phenylmethyl)-4-piperidinyl]ethyl]pyrrolo[3,4-b](benzo[b]-thieno)1H-3-one;

2,3-dihydro-5-methyl-2-[[1-(phenylmethyl)-4-piperidinyl]methylene]-1H-cyclopent[b](benzo[b]-thieno)-1-one;

2,3-dihydro-5-methyl-2-[[1-(phenylmethyl)-4-piperidinyl]methyl]-1H-cyclopent[b](benzo[b]-thieno)-1-one.

3. A pharmaceutical composition comprising a compound according to claim 1 or a pharmaceutically acceptable salt thereof, and a pharmaceutically acceptable carrier.

4. A method of inhibiting cholinesterase in a mammal, comprising administering to a mammal a cholinesterase inhibiting amount of a compound according to claim 1, or a pharmaceutically salt therof.

5. A method of enhancing memory comprising administering to a patient a memory enhancing effective amount of a compound according to claim 1, or a pharmaceutically acceptable salt thereof.

* * * * *